(12) United States Patent
Bourdoulous et al.

(10) Patent No.: US 11,814,685 B2
(45) Date of Patent: Nov. 14, 2023

(54) DIAGNOSIS AND/OR PROGNOSIS OF HER2-DEPENDENT CANCER USING ONE OR MORE MIRNA AS A BIOMARKER

(71) Applicants: UNIVERSITÉ PARIS CITÉ, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S.), Paris (FR)

(72) Inventors: Sandrine Bourdoulous, Gagny (FR); Anaïs Domingot, Paris (FR); Camille Faure, Paris (FR)

(73) Assignees: UNIVERSITÉ PARIS CITÉ, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 427 days.

(21) Appl. No.: 16/758,624

(22) PCT Filed: Oct. 24, 2018

(86) PCT No.: PCT/EP2018/079215
§ 371 (c)(1),
(2) Date: Apr. 23, 2020

(87) PCT Pub. No.: WO2019/081610
PCT Pub. Date: May 2, 2019

(65) Prior Publication Data
US 2020/0347457 A1    Nov. 5, 2020

(30) Foreign Application Priority Data
Oct. 24, 2017 (EP) ................. 17306464

(51) Int. Cl.
*C12Q 1/6886* (2018.01)
(52) U.S. Cl.
CPC ...... *C12Q 1/6886* (2013.01); *C12Q 2600/118* (2013.01); *C12Q 2600/158* (2013.01); *C12Q 2600/178* (2013.01)
(58) Field of Classification Search
CPC ............ C12Q 1/6886; C12Q 2600/118; C12Q 2600/158; C12Q 2600/178
See application file for complete search history.

(56) References Cited

U.S. PATENT DOCUMENTS

| 2012/0264131 A1 | 10/2012 | Goel et al. |
| 2013/0178383 A1 | 7/2013 | Spetzler et al. |
| 2014/0274769 A1 | 9/2014 | Wang et al. |
| 2017/0016076 A1 | 1/2017 | Barnett-Itzhaki et al. |

FOREIGN PATENT DOCUMENTS

| CN | 106636316 A | 5/2017 |
| EP | 2924126 A1 | 9/2015 |
| WO | 2015/056195 A1 | 4/2015 |
| WO | 2016/144265 A1 | 9/2016 |
| WO | 2017/057312 A1 | 4/2017 |

OTHER PUBLICATIONS

Kolacinska et al. (DNA and Cell Biol. (2014) 33(9):624-629). (Year: 2014).*
International Search Report and Written Opinion dated Jan. 28, 2019 from International Application No. PCTEP2018/079215 (Authorized Officer, Jan Gabriels), 20 pages.
Luo et al., "Elevated microRNA-125b levels predict a worse prognosis in HER2-positive breast cancer patients", Oncology Letters, 2016, vol. 13, No. 2, pp. 867-874.
Williams et al., "Quantification of microRNAs directly from body fluids using a base-stacking isothermal amplification method in a point-of-care device", Biomedical Microdevices, 2017, vol. 19, No. 3, 8 pages.
Bagnoli et al., "Development and validation of a microRNA-based signature (MiROvaR) to predict early relapse or progression of epithelilal ovarian cancer: a cohort study", The Lancet Oncology, 2016, vol. 17, No. 8, pp. 1137-1146.
Katz et al., "MicroRNAs in Ovarian Cancer", Human Pathology, 2015, vol. 46, No. 9, pp. 1245-1256.
Singh et al., "Targeted Stage-Specific Inflammatory microRNA Profiling in Urine During Disease Progression in Experimental Autoimmune Encephalomyelitis: Markers of Disease Progression and Drug Response", Journal of Neuroimmune Pharmacology, 2016, vol. 11, No. 1, pp. 84-97.

* cited by examiner

*Primary Examiner* — J. E. Angell
(74) *Attorney, Agent, or Firm* — MH2 TECHNOLOGY LAW GROUP, LLP

(57) ABSTRACT

This invention relates to a method for diagnosing and/or prognosticating HER2-dependent cancer in a subject, comprising a) measuring the amount of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p in a sample from the subject; b) comparing the amount of one or more miRNA measured in step a) to a reference value; c) finding a deviation or no deviation of the amount of one or more miRNA measured in step a) from the reference value; and d) attributing said finding of deviation or no deviation to a particular diagnosis and/or prognosis of HER2-dependent cancer in the subject.

15 Claims, 14 Drawing Sheets
Specification includes a Sequence Listing.

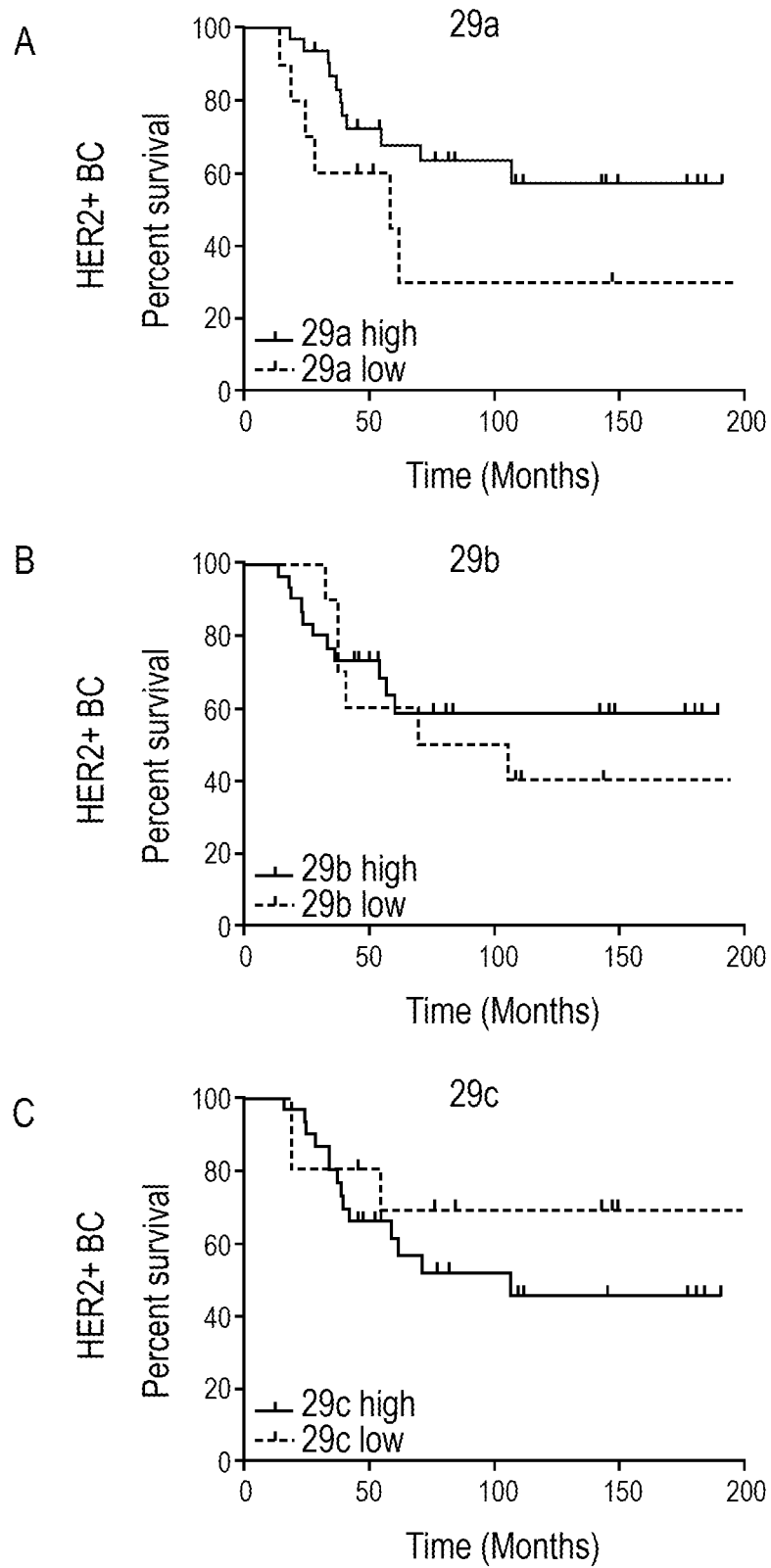

DIAGNOSIS AND/OR PROGNOSIS OF HER2-DEPENDENT CANCER USING ONE OR MORE MIRNA AS A BIOMARKER

CROSS-REFERENCE TO RELATED APPLICATIONS

This application is a U.S. National Stage Application of International Application No. PCT/EP2018/079215, filed on Oct. 24, 2018, which claims priority to European Patent Application No. 17306464.3, filed on Oct. 24, 2017, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 23, 2020, is named 1h316870_0006_st25_pct.txt and is 3 kilobytes in size.

BACKGROUND OF THE INVENTION

Breast cancer is the most common cancer in women worldwide, with nearly 1.7 million new cases diagnosed in 2012 (second most common cancer overall). This represents about 12% of all new cancer cases and 25% of all cancers in women. About half the breast cancer cases and 60% of the deaths are estimated to occur in economically developing countries. The rate of incidence observed in France is among the strongest in Europe and is in constant increase.

About 20 to 30% of primary human breast cancers are due to the deregulated expression of HER2: it represents approximately 8,000 patients a year in France and 450,000 patients a year worldwide. HER2 is a well-known member of the human epidermal growth factor receptor (HER/EGFR/ERBB) family. ErbB2 overexpression is associated with a poor diagnosis: tumors with deregulated HER2 have been shown to grow faster to be more aggressive and to be less sensitive to chemotherapy or to hormonotherapy. HER2 deregulation is also associated with disease recurrence. Then, so called HER2-dependent cancer constitute a very specific group of cancer of an utmost interest in public health. Indeed, only 25% of the treated patients respond to the actual therapies. The actual strategies aiming at targeting the extracellular domain of HER2 (anti-HER2 antibody therapies such as Herceptin/Trastuzumab, Pertuzumab and the recently developed Trastuzumab emtansine from Genentech, USA) or the kinase activity of the receptor (small molecule tyrosine kinase inhibitors, such as Lapatinib/Tykerb, GSK, USA) have proven to exhibit limited actions.

In particular, these molecules have no potent action on the mutated and truncated forms of HER2. Concerning Trastuzumab, 66% to 88% of treated patients never respond to treatment (i.e. present a "primary resistance") and among the one-third of the treated patients that respond to this agent, a disease progression on average in less than one year (i.e. develop an "acquired resistance") is generally observed. The efficacy is limited by the development of therapeutic resistance mainly attributed to the expression of p95HER-2, as this highly active truncated form of HER2 lacks the recognition site for Trastuzumab.

Generally, HER2 (over)expression is established as a marker of poor prognosis in breast cancer. Different techniques have been developed to evaluate if a cancer/patient is "positive" for HERZ (i.e. HER2+) or "negative" for HER2 (i.e. HER2–), such as fluorescence in situ hybridization (FISH) test or immunohistochemistry (IHC test).

However, there is a need for developing new methods for the diagnostic and/or prognostic of HER2-dependent cancer, such as HER2+ breast cancer.

The Applicant has identified compounds, micro ribonucleic acids (miRNAs), which constitute a new approach for the diagnostic and/or prognostic of HER2-dependent cancers. In particular, the inventors have identified a strong functional link between specific miRNAs and HER2 genes and found that the diagnosis of HER2-dependent cancer or a poor prognosis of HER2-dependent cancer is specifically associated with a level of these miRNA.

This finding makes it possible to develop a new method for diagnosing and/or prognosticating HER2-dependent cancer in a subject.

SUMMARY OF THE INVENTION

The inventors therefore propose here a method for the diagnostic and/or prognosis wherein the amount of one or more specific miRNA in the sample from a subject compared to a reference value represents the prediction of HER2-dependent cancer or represents a prognosis for HER2-dependent cancer, indicating that the subject has a risk or no of having and/or developing HER2-dependent cancer.

The invention relates to a method for diagnosing and/or prognosticating HER2-dependent cancer in a subject, comprising:
  a) measuring the amount of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p in a sample from the subject;
  b) comparing the amount of one or more miRNA measured in step a) to a reference value;
  c) finding a deviation or no deviation of the amount of one or more miRNA measured in step a) from the reference value; and
  d) attributing said finding of deviation or no deviation to a particular diagnosis and/or prognosis of HER2-dependent cancer in the subject.

The invention also relates to a method for monitoring a change in the diagnosis and/or prognosis of HER2-dependent cancer in a subject, comprising:
  a) applying the method for diagnosing and/or prognosticating HER2-dependent cancer to the subject at one or more successive time points, whereby the diagnosis and/or prognosis of HER2-dependent cancer in the subject is determined at said successive time points;
  b) comparing the diagnosis and/or prognosis of HER2-dependent cancer in the subject at said successive time points as determined in step a); and
  c) finding the presence or absence of a change between the diagnosis of HER2-dependent cancer in the subject at said successive time points as determined in step a).

The invention also relates to a kit for determining the diagnostic and/or the prognosis of HER2+ breast cancer in a subject suffering thereof, comprising specific amplification primers and/or probes for the specific quantitative amplification of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p.

DETAILED DESCRIPTION OF THE INVENTION

Definitions

The terms "diagnosing" or "diagnosis" and "prognosticating" or "prognosis", as used herein, are used in the broadest sense, and are commonly used and are well-understood in medical and clinical practice. By means of further explanation and without limitation, "prognosticating" or "prognosis" refers to the determination of probability, risk or possibility of developing HER2-dependent cancer in a subject. By means of further explanation and without limitation, "diagnosing" or "diagnosis" refers to the determination of a probability or a possibility of having HER2-dependent cancer in a subject.

The term "HER2", as used herein, refers to "Human Epidermal growth factor Receptor 2" which is a protein member of the human epidermal growth factor receptor family. "HER2" is also frequently called "ErbB2". "ErbB2" and "HER2" are used interchangeably in the present invention.

The term "HER2-dependent cancer" or "HER2 positive cancer" or "HER2+ cancer", as used herein, refers to cancer involving exacerbated HER2 activation. In particular, the term "HER2-dependent cancer" refers to any cancer case for which cancer cells exhibiting a deregulation of HER2 gene have been identified, in opposition to "HER2-independent cancer" or "HER2 negative cancer" or "HER2– cancer". More particularly said deregulation can correspond to an amplification of HER2 gene. This amplification can be detected at the genetic level, or at the protein level. For example, guidelines emitted by the American society of Clinical Oncology/College of American Pathologists (ASCO/CAP) for breast cancer set several cut-offs for determining the ErbB2 status of breast cancer. These guidelines prescribe that a cancer should be considered as "HER2-dependent" if, for the primary site and if possible for the metastatic site:
  a uniform and intense membrane staining of more than 30% of invasive tumor cells is observed in immunochemistry (IHC), or
  i) a FISH amplified ratio of HER2 to CEP17 (chromosome 17 centromere) superior or equal to 2 (dual probe testing) or ii) a FISH amplified ratio of HER2 to CEP17 (chromosome 17 centromere) inferior to 2 (dual probe testing) with an average HER2 copy number of at least 6 copies per nucleus (single probe testing) is determined, or iii) a single probe average of at least 6 signals for the HER2 copy number per cells.

Besides, a cancer is considered as "HER2-independent" when, for the primary site and if possible for the metastatic site:
  in IHC, no staining or a weak incomplete membrane staining, or a weak but complete membrane staining is observed in less than 10% of cells, or
  the FISH HER2/CEP17 ratio inferior to 2 with an average copy number of HER2 inferior to 4 signals per cells is noticed (dual probe testing), or an average copy number of HER2 inferior to 4 signals per cell is noticed (in cases where a single probe is used).

The HER2 status will be considered as equivocal (then a new test should be performed) when, for the primary site and, if possible, for the metastatic site:
  in IHC, i) an incomplete labelling of circumferential membrane and/or weak/moderate labelling is noticed but within superior to 10% of the invasive tumor cells or ii) a complete and intense labelling of circumferential membrane is noticed but for 10% or less of the invasive tumor cells, or
  the FISH HER2/CEP17 ratio inferior to 2 with an average copy number of HER2 of at least 4 signals but less than 6 signals per cell is noticed (dual probe testing), or an average copy number of HER2 of at least 4 signals but less than 6 signals per cell is noticed (in cases where a single probe is used).

Deregulation of HER2 gene can also correspond to activating mutations in HER2 gene disregarding its copy number, leading to an increase of the tyrosine kinase activity of HER2. For example, said activating mutations can be V659E, G309A, D769H, D769Y, V777L, P780ins, V842I, R896C, K753E or L755S and can be detected by Polymerase Chain Reaction or any sequencing technique [Bose et al. Cancer Discov. 2013, 3(2), 224-237; Zuo et al. Clin Cancer Res 2016, 22(19), 4859-4869]. Also, both an amplification of HER2 gene and a somatic activating mutation can be detected in the same case of cancer.

Well known molecular biology tests other than Fish or IHC, using negative and positive control cells with an established HER2 status, can be used for determining the HER2 status of a cancer by way of comparison, as for example Enzyme-Linked Immunosorbent Assays, Western blotting assays, Polymerase Chain Reaction, etc.

Preferably, the HER2-dependent cancer according to the invention is selected from the group consisting of breast cancer, female genital tract cancer, such as endometrial cancer, uterine cancer or ovarian cancer, bladder cancer, anal cancer, colorectal cancer, in particular uterine serous cancer, such as uterine papillary serous carcinoma, lung cancer, in particular non-small-cell lung cancer, liver cancer, kidney cancer, gastroesophageal cancer, stomach cancer, pancreas cancer and gastric cancer. In a preferred embodiment, the HER2-dependent cancer may be HER2+ breast cancer, HER2+ ovarian cancer, HER2+ bladder cancer, HER2+ colorectal cancer, HER2+ uterine papillary serous carcinoma and HER2+ gastric cancer, preferably HER2+ breast cancer.

For the purposes of the invention, the term "marker" (or "biomarker") is an entity, such as a nucleic acid (e.g. miRNA), which can be used for the diagnosis and/or prognosis of HER2-dependent cancer. According to the invention, the biomarker may be a miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p.

The term "micro ribonucleic acid" or "miRNA", as used herein, refers to a small non-coding RNA molecule (generally containing about 18-25 nucleotides) found in plants, animals and some viruses, that functions in RNA silencing and post-transcriptional regulation of gene expression. The miRNA according to the invention may be located within the cell or may be located in the extracellular environment. The latter are generally known as circulating miRNA or extracellular miRNA.

The term "patient" or "subject", as used herein, refers to a human or non-human mammal (such as a rodent (mouse, rat), a feline, a canine, or a primate) affected or likely to be affected with HER2-dependent cancer. Preferably, the subject is a human, man or woman. Preferably, the subject is HER2+.

The term "sample" or "biological sample", as used herein, includes any biological specimen obtained from a subject, such as a tumor sample or a body fluid sample. A body fluid sample may be selected from the group consisting of blood, serum plasma, saliva, urine, amniotic fluid, breast milk, bronchial lavage, cerebrospinal fluid, peritoneal fluid, seminal fluid, tears and pleural fluid, preferably blood. A tumor sample may include biopsies, such as tumor biopsies. Preferred samples may include ones comprising one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p in detectable quantities.

The term "reference value" or "reference profile" means a value or profile representing (i) a diagnosis of no HER2-dependent cancer, (ii) a diagnosis of HER2-dependent cancer, (iii) a good prognosis of HER2-dependent cancer or (iv) a bad prognosis of HER2-dependent cancer. For example, a reference value for the amount of a miRNA may be obtained as follows:
a) measuring the amount of miRNA in:
   a1) one or more samples from one or more subjects not having HER2-dependent cancer, or
   a2) one or more samples from one or more subjects having HER2-dependent cancer, and
b) storing the quantity of miRNA
   b1) as measured in (a1) as the reference value representing the diagnosis and/or prognosis of no HER2-dependent cancer, or
   b2) as measured in (a2) as the reference value representing the diagnosis and/or prognosis of HER2-dependent cancer.

A reference value also encompasses a reference range.

The terms "amount", "quantity", and "level" are synonymous and generally well-understood in the art. The terms as used herein may particularly refer to an absolute quantification of a biomarker in a sample, or to a relative quantification of a biomarker in a sample (i.e. relative to another value such as relative to a reference value as taught herein), or to a range of values indicating a base-line expression of the biomarker. These values or ranges can be obtained from a single patient or from a group of patients. An absolute quantity of a biomarker in a sample may be advantageously expressed as weight or as molar amount, or more commonly as a concentration. A relative quantity of a biomarker in a sample may be advantageously expressed as an increase or a decrease relative to (i.e. compared to) another value, such as relative to (i.e. compared to) a reference value.

The term "expression profile", as used herein, designates the amount of a group of at least two miRNA chosen in the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5$_p$, miRNA 615-3p, miRNA 451a-3p and miRNA 542-5p.

The term "deviation" of a first value from a second value may generally encompass any direction, such as increase or decrease of a first value compared to a second value.

The term "treating" or "treatment" means reversing, alleviating, inhibiting the progress of, or preventing the disorder or condition to which such term applies, or one or more symptoms of such disorder or condition. In particular, the treatment of the disorder may consist in destroying, depleting or inhibiting the proliferation of cancer cells. Most preferably, such treatment leads to the complete depletion of cancer cells.

Diagnosis and/or Prognosis

The present invention results from the advantages highlighted by the inventors that the increase or decrease of the amount of one or more specific miRNA makes it possible to diagnose and/or prognose HER2-dependent cancer. The resulting applications are described below.

The invention relates to a method for diagnosing and/or prognosticating HER2-dependent cancer in a subject, comprising:
a) measuring the amount of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p in a sample from the subject;
b) comparing the amount of one or more miRNA measured in step a) to a reference value;
c) finding a deviation or no deviation of the amount of one or more miRNA measured in step a) from the reference value; and
d) attributing said finding of deviation or no deviation to a particular diagnosis and/or prognosis of HER2-dependent cancer in the subject.

In some embodiments, said miRNA is a human miRNA as detailed in Table 1.

TABLE 1 miRNA measured in the method of the invention

| miRNA | Detailed name | Nucleotide sequence | Reference (miRBase) | SEQ ID NO: |
|---|---|---|---|---|
| miRNA-429-3p | hsa-RNA-429-3p | uagcaccaucugaaaucgguua | MIMAT0001536 | 1 |
| miRNA 29c-3p | hsa-miRNA 29c-3p | uagcaccauuugaaaucgguua | MIMAT0000681 | 2 |
| miRNA 29a-3p | hsa-miRNA 29a-3p | uagcaccaucugaaaucgguua | MIMAT0000086 | 3 |
| miRNA 29b-3p | hsa-miRNA 29b1-3p<br>hsa-miRNA 29b2-3p | uagcaccauuugaaaucaguguu | MIMAT0000100 | 4 |

TABLE 1-continued miRNA measured in the method of the invention

| miRNA | Detailed name | Nucleotide sequence | Reference (miRBase) | SEQ ID NO: |
|---|---|---|---|---|
| miRNA 200a-3p | hsa-miRNA-200a-3p | uaacacugucugguaacgaugu | MIMAT0000682 | 5 |
| miRNA 200b-3p | hsa-miRNA-200b-3p | uaauacugccugguaaugauga | MIMAT0000318 | 6 |
| miRNA 200c-3p | hsa-miRNA-200c-3p | uaauacugccggguaaugauga | MIMAT0000617 | 7 |
| miRNA 141-3p | hsa-miRNA-141-3p | uaacacugucugguaaagaugg | MIMAT0000432 | 8 |
| miRNA 15a-5p | hsa-miRNA 15a-5p | uagcagcacauaaugguuugug | MIMAT0000068 | 9 |
| miRNA 15b-5p | hsa-miRNA 15b-5p | uagcagcacaucaugguuuaca | MIMAT0000417 | 10 |
| miRNA 16-5p | hsa-miRNA 16-5p | uagcagcacguaaauauuggcg | MIMAT0000069 | 11 |
| miRNA 424-5p | hsa-miRNA-424-5p | cagcagcaauucauguuuugaa | MIMAT0001341 | 12 |
| miRNA 497-5p | hsa-miRNA-497-5p | cagcagcacacugugguuugu | MIMAT0002820 | 13 |
| miRNA 615-3p | hsa-miRNA-615-3p | uccgagccugggucucccucuu | MIMAT0003283 | 14 |
| miRNA 451a-3p | hsa-miRNA-451a-3p | aaaccguuaccauuacugaguu | MIMAT0001631 | 15 |
| miRNA 542-5p | hsa-miRNA-542-5p | ucggggaucaucaugucacgaga | MIMAT0003340 | 16 |

The methods of the invention may be used in individuals who have not yet been diagnosed as having HER2-dependent cancer (for example, preventative screening), or who have been diagnosed as having HER2-dependent cancer, or who are suspected of having HER2-dependent cancer (for example, display one or more symptoms characteristic of HER2-dependent cancer), or who are at risk of developing HER2-dependent cancer. The methods may also be used to detect various stages of progression or severity of HER2-dependent cancer.

Step a)

Step a) is the measure the amount of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p in a sample from the subject.

In one embodiment, step a) is the measure of the amount of two or more of the above listed miRNA, for example 3, 4, 5, 6, 7, 8, 9 10, 11, 12, 13, 14, 15, 16 of the above listed miRNA. In this embodiment, step a) may be the measure of the expression profile comprising at least two of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p, for example 3, 4, 5, 6, 7, 8, 9 10, 11, 12, 13, 14, 15, 16 of the above listed miRNA.

Accordingly, the invention therefore relates to a method for diagnosing and/or prognosticating HER2-dependent cancer in a subject, comprising:

a) measuring the expression profile comprising two or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p in a sample from the subject;

b) comparing said expression profile measured in step a) to a reference profile;

c) finding a deviation or no deviation of the expression profile measured in step a) from the reference profile; and d) attributing said finding of deviation or no deviation to a particular diagnosis and/or prognosis of HER2-dependent cancer in the subject.

The amount of the one or more miRNA (or expression profile) may be measured by any suitable technique known in the prior art. In some embodiments, the amount of each miRNA may be measured directly on extracted miRNA sample. From the miRNA sample, the amount of a miRNA may be measured using any technology known by a man skilled in the art, including microarrays or quantitative PCR (qPCR)

In a preferred embodiment, the amount of a miRNA (or expression profile) may be measured by the use of qPCR (e.g. real-time PCT (RT-PCR)). Quantitative PCR is a well-known and easily available technology for those skilled in the art and does therefore not need a precise description. In particular, a skilled person knows how to design specific probes for a PCR amplification of a miRNA in view of the sequence of said miRNA.

In another embodiment, the expression levels of a miRNA (or expression profile) may be measured by the use of nucleic microarrays. Basically, to determine the amount of the one or more miRNA (or expression profile) in a miRNA sample, said sample can be labelled, contacted with the microarray in hybridization conditions, leading to the formation of complexes between miRNA that are complementary to probe sequences attached to the microarray surface. The presence of labelled hybridized complexes can then be detected using standard techniques.

Step b) & c)

Step b) and c) is the comparison of the amount of one or more miRNA measured in step a) to a corresponding reference value(s) and the finding of a deviation or no deviation of the amount of one or more miRNA measured in step a) from the corresponding reference value(s).

In one embodiment, step b) and c) may be the comparison of said expression profile measured in step a) to a reference profile and the finding of a deviation or no deviation of the expression profile measured in step a) from the reference profile.

A deviation of the amount of one or more miRNA may encompass a decrease of the amount of one or more miRNA compared to the corresponding reference value(s) or an increase of the amount of one or more miRNA compared to the corresponding reference value(s).

For example, a deviation of the amount of a miRNA compared to the reference value may encompass a decrease of at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), or more compared to the reference value.

For example, a deviation of the amount of a miRNA compared to the reference value may encompass an increase of at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 900% (about 10-fold or more), or more, compared to a reference value.

In a preferred embodiment, the amount of the one or more miRNA in the sample from the subject is at least 1.5-fold increased compared to the reference value, more preferably at least 2-fold increased.

In another preferred embodiment, the amount of the one or more miRNA in the sample from the subject is at least 0.5-fold decreased compared to the reference value, more preferably at least 0.7-fold decreased.

Step d)

Step d) is the attribution of the finding of deviation or no deviation to a particular diagnosis and/or prognosis of HER2-dependent cancer in the subject.

A deviation which is an increase of the amount of one or more miRNA selected from the group consisting of miRNA 429-3p, miRNA 29c-3p, miRNA 200a-3p, miRNA 200b-3p, miRNA 200c-3p, miRNA 497-5p, miRNA 615-3p, miRNA 451a-3p and miRNA 542-5p, miRNA 15a-5p, miRNA 16-5p and miRNA 424-5p compared to the corresponding reference value(s) represents the diagnosis of HER2-dependent cancer or represents a bad prognosis for HER2-dependent cancer. Accordingly, a higher amount of one or more miRNA selected from the group consisting of miRNA 429-3p, miRNA 29c-3p, miRNA 200a-3p, miRNA 200b-3p, miRNA 200c-3p, miRNA 497-5p, miRNA 615-3p, miRNA 451a-3p and miRNA 542-5p, miRNA 15a-5p, miRNA 16-5p and miRNA 424-5p in the sample from the subject compared to the corresponding reference value(s) indicates that the subject has HER2-dependent cancer or indicates a short-term survival of said subject.

A deviation which is a decrease of the amount of one or more miRNA selected from the group consisting of miRNA 429-3p, miRNA 29c-3p, miRNA 200a-3p, miRNA 200b-3p, miRNA 200c-3p, miRNA 497-5p, miRNA 615-3p, miRNA 451a-3p and miRNA 542-5p, miRNA 15a-5p, miRNA 16-5p and miRNA 424-5p compared to the corresponding reference value(s) represents the diagnosis of no HER2-dependent cancer or represents a good prognosis for HER2-dependent cancer. Accordingly, a lower amount of one or more miRNA selected from the group consisting of miRNA 429-3p, miRNA 29c-3p, miRNA 200a-3p, miRNA 200b-3p, miRNA 200c-3p, miRNA 497-5p, miRNA 615-3p, miRNA 451a-3p and miRNA 542-5p, miRNA 15a-5p, miRNA 16-5p and miRNA 424-5p in the sample from the subject compared to the corresponding reference value(s) indicates that the subject has no HER2-dependent cancer or indicates a long-term survival of said subject.

A deviation which is a decrease of the amount of one or more miRNA selected from the group consisting of miRNA 29a-3p, miRNA 29b-3p and miRNA 15b compared to the corresponding reference value(s) represents the diagnosis of HER2-dependent cancer or represents a bad prognosis for HER2-dependent cancer. Accordingly, a lower amount of one or more miRNA selected from the group consisting of miRNA 29a-3p, miRNA 29b-3p and miRNA 15b in the sample from the subject compared to the corresponding reference value(s) indicates that the subject has HER2-dependent cancer and/or indicates a short-term survival of said subject.

A deviation which is an increase of the amount of one or more miRNA selected from the group consisting of miRNA 29a-3p, miRNA 29b-3p and miRNA 15b compared to the corresponding reference value(s) represents the diagnosis of no HER2-dependent cancer or represents a good prognosis for HER2-dependent cancer. Accordingly, a higher amount of one or more miRNA selected from the group consisting of miRNA 29a-3p, miRNA 29b-3p and miRNA 15b in the sample from the subject compared to the corresponding reference value(s) indicates that the subject has no HER2-dependent cancer and/or indicates a long-term survival of said subject.

When no deviation is found between the amount of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p and a corresponding reference value(s), the absence of such deviation is indicative of or may be attributed to the conclusion that the diagnosis and/or prognosis of HER2-dependent cancer is substantially the same as that represented by the corresponding reference value(s).

As shown in the experimental section some of the miRNAs are all the more of interest as they are specifically associated with life expectancy, specifically in HER2+ cancer. Accordingly in a specific embodiment the invention relates to a method for prognosticating HER2-dependent cancer in a subject, comprising:

a) measuring the amount of one or more miRNA selected from the group consisting of miRNA 429-3p, miRNA 29c-3p, miRNA 200b-3p, miRNA 15a-5p, miRNA 16-5p, miRNA 424-5p, miRNA 497-5p, miRNA 615-3p, miRNA 451a-3p and miRNA 542-5p in a sample from the subject;
b) comparing the amount of one or more miRNA measured in step a) to a reference value;
c) finding a deviation or no deviation of the amount of one or more miRNA measured in step a) from the reference value; and
d) attributing said finding of deviation or no deviation to a particular prognosis of HER2-dependent cancer in the subject.

As also shown in the experimental section, the amount of miRNA 141-3p, miRNA 200a-3p, miRNA 200b-3p and miRNA 200c-3p is significantly and specifically increased in the serum of HER2+ cancer patients compared to HER2− cancer patients and healthy individuals. Therefore, in an embodiment the invention relates to a method for diagnosing and/or prognosticating HER2-dependent cancer in a subject, comprising:
a) measuring the amount of at least miRNA 141-3p, miRNA 200a-3p, miRNA 200b-3p and miRNA 200c-3p in a sample from the subject;
b) comparing the amount of one or more miRNA measured in step a) to a reference value;
c) finding a deviation or no deviation of the amount of one or more miRNA measured in step a) from the reference value; and
d) attributing said finding of deviation or no deviation to a particular diagnosis and/or prognosis of HER2-dependent cancer in the subject.

The methods of the invention may also be combined with the assessment of one or more further biomarkers relevant for HER2-dependent cancer.

The one or more biomarkers may be chosen from the group consisting of ER/PR (Estrogen Receptor/Progesterone Receptor), HER2, p95HER2, moesin (MSN), KI67, TOP2A (Topoisomerase 2-alpha), BCL2 (B-cell lymphoma 2), GSTM1 (Glutathione S-Transferase Mu 1), BAG1, Cyclin B1, cathepsin L2, CD68 and TP53.

A Method for Monitoring a Change in the Diagnosis and/or Prognosis

The method for diagnosing and/or prognosticating HER2-dependent cancer in a subject may also be used to detect response of HER2-dependent cancer to prophylactic or therapeutic treatments or other interventions, e.g. by performing the methods at different time points during said prophylactic or therapeutic treatment or other intervention.

The invention therefore relates to a method for monitoring a change in the diagnosis and/or prognosis of HER2-dependent cancer in a subject, comprising:
a) applying the method of any of claims 1 to 11 to the subject at one or more successive time points, whereby the diagnosis and/or prognosis of HER2-dependent cancer in the subject is determined at said successive time points;
b) comparing the diagnosis and/or prognosis of HER2-dependent cancer in the subject at said successive time points as determined in step a); and
c) finding the presence or absence of a change between the diagnosis of HER2-dependent cancer in the subject at said successive time points as determined in step a).

In some embodiments, said change in the diagnosis and/or prognosis of HER2-dependent cancer in the subject is monitored in the course of a medical treatment of said subject.

The medical treatment may be a prophylactic treatment or a therapeutic treatment, preferably an antitumoral treatment. The antitumoral treatment may be any treatment known for the treatment of said HER2-dependent cancer. For example, the antitumoral treatment may aim at targeting the extracellular domain of HER2, such as anti-HER2 antibody therapies, for example Herceptin/Trastuzumab, Pertuzumab and Trastuzumab emtansine (Genentech, USA); or the antitumoral treatment may aim at targeting the kinase activity of HER2, such as small molecule tyrosine kinase inhibitors, for example, Neratinib, Tucatinib or, Lapatinib/Tykerb (GSK, USA). The antitumoral treatment may also be a taxane-based chemotherapy, such as paclitaxel.

Kit

The invention also relates to a kit for determining the diagnostic and/or the prognosis of HER2+ breast cancer in a subject suffering thereof, comprising specific amplification primers and/or probes for the specific quantitative amplification of one or more miRNA selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-3p and miRNA 542-5p.

The invention also relates to a kit for determining the prognosis of HER2+ cancer in a subject suffering thereof, comprising specific amplification primers and/or probes for the specific quantitative amplification for measuring the amount of one or more miRNA selected from the group consisting of miRNA 429-3p, miRNA 29c-3p, miRNA 200b-3p, miRNA 15a-5p, miRNA 16-5p, miRNA 424-5p, miRNA 497-5p, miRNA 615-3p, miRNA 451a-3p and miRNA 542-5p.

The invention further relates to a kit for determining the diagnostic and/or the prognosis of HER2+ cancer in a subject suffering thereof, comprising specific amplification primers and/or probes for the specific quantitative amplification of miRNA selected from the group consisting of miRNA 141-3p, miRNA 200a-3p, miRNA 200b-3p and miRNA 200c-3p.

Method of Treatment

As described above, the present invention is useful to detect response of HER2-dependent cancer to prophylactic or therapeutic treatments or other interventions, e.g. by performing the methods at different time points during said prophylactic or therapeutic treatment or other intervention.

Similarly, the present invention also relates to a method of treating HER2-dependent cancer in a subject, comprising:
(i) the implementation of a diagnostic or prognostic method according to the invention, and
(ii) when the method indicates that the subject has HER2-dependent cancer and/or indicates a short-term survival of said subject, institute appropriate treatment in said subject.

In one particular embodiment, said appropriate treatment is one or more medicines selected from a prophylactic treatment or a therapeutic treatment, preferably an antitumoral treatment aiming at targeting the extracellular domain of HER2, such as anti-HER2 antibody therapies, for example Herceptin/Trastuzumab, Pertuzumab and Trastuzumab emtansine (Genentech, USA) or aiming at targeting the kinase activity of HER2, such as small molecule tyrosine kinase inhibitors, for example Neratinib, Tucatinib or Lapatinib/Tykerb (GSK, USA).

The following examples illustrate the present invention without limiting the scope of the invention to said examples.

FIGURES

FIG. 1 represents miRnome analysis of breast cancer cell lines with different HER2/MSN status. Transcriptome analysis showing the level of HER2 mRNA expression in breast cancer cell lines is shown in the top panel. Representation of candidate miRNAs expression is shown in the bottom panel.

MSN$^{hi}$ means high expression of MSN.

MSN$^{lo}$ means low expression of MSN.

Figure 6:
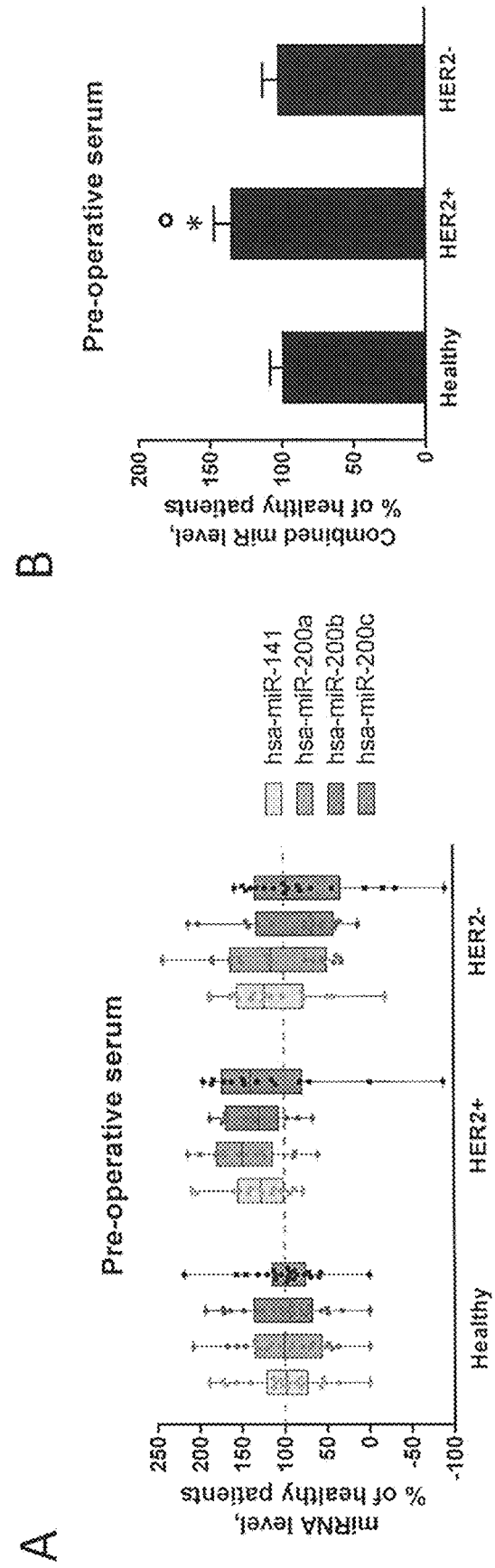

FIG. 6 represents the level of expression of miR-141-3p, miR-200a-3p, miR-200b-3p, miR-200c-3p in pre-operative serum samples derived from healthy individuals (n=22), HER2+ breast cancer patients (n=14) or HER2− breast cancer patients (n=18). Individual miRNA level of expression is shown in the left panel. Combined miRNA level of expression is shown in the right panel.

In the figures and examples "miR" and "miRNA" are used interchangeably, e.g. "miR 429-3p" means "miRNA 429-3p".

EXAMPLES

Example 1

Methods

Methods:

Datasets and Survival analysis

The effect of miRNAs on the overall survival of breast cancer patients was measured using miRpower [Breast] (http://kmplot.com/analysis/index.php?p=service&cancer=breast_miRna) on the METABRIC (1262 breast tumors). Analyses were either performed on HER2 positive status (HER2+ by Immunohisto chemistry (IHC) on molecular subtype HER2+ ER) or performed on HER2− (Triple negative breast cancers (TNBC) molecular subtype) breast cancer patients.

The level of expression of miR-141-3p, miR-200a-3p, miR-200b-3p, miR-200c-3p in pre-operative serum samples derived from healthy individuals (n=22), HER2+ breast cancer patients (n=14) or HER2− breast cancer patients (n=18) was obtained from the study GSE42128 (Gene Expression Omnibus accession number) on array express database (http://www.ebi.ac.uk/arrayexpress/). miRNA expression was normalized to the mean value of corresponding Healthy controls. The mean value of their combined expression is also shown (FIG. 6).

Cell Lines

The HER2 and MSN mRNA level analysis was performed on 25 breast cancer cell lines with various HER2 status: MDA-MB-361 (ATCC HTB-27), BT-483 (ATCC HTB-121), MDA-MB-453 (ATCC HTB-131), MDA-MB-415 (ATCC HTB-128), ZR-75-1 (ATCC CRL-1500), HCC202 (ATCC CRL-2316), BT-474 (ATCC HTB-20), MCF 10A (ATCC CRL-10317), MCF-12A (ATCC CRL-10782), MDA-MB-436 ATCC HTB-130, hTERT-HME1 (ATCC, CRL-4010), MCF-10-2A (ATCC CRL-10781), 184B5 (ATCC CRL-8799), BT-549 (ATCC HTB-122), HCC1937 (ATCC CRL-2336), Hs 578T (ATCC HTB-126), MDA-MB-231 (ATCC HTB-26), MCF-12F (ATCC CRL-10783), PMC42 (RRID:CVCL_5215), MDA-MB-157 (ATCC HTB-24), BT-20 (ATCC HTB-19), HCC70 (ATCC CRL-2315), HCC1599 (ATCC CRL-2331), HCC1143 (ATCC CRL-2321) and HCC1187 (ATCC CRL-2322).

miRNome

MiRNA expression levels in samples were quantified by quantitative RT-PCR (RT-qPCR) using the SYBR Green Master Mix kit on the ABI Prism 7900 Sequence Detection System (Perkin-Elmer Applied Biosystems, Foster City, Calif., USA). The Human miScript Primer Assays version 9.0 and 11.0 from Qiagen, designed to detect 804 human miRNA probes, were used according to the manufacturer's guidelines. Small nucleolar RNA RNU44 (Qiagen) was used as endogenous control to normalize miRNA expression levels. The relative expression level of each miRNA, expressed as N-fold difference in target miRNA expression relative to RNU44, and termed "Ntarget", was calculated as follows: Ntarget=2ΔCtsample. The value of the cycle threshold (ΔCt) of a given sample was determined by subtracting the Ct value of the target miRNA from the average Ct value of RNU44. The Ntarget values of samples were subsequently normalized such that the median Ntarget value of normal breast samples was one. The relative expression of each miRNA was characterized by the median and the range, and a non-parametric Mann-Whitney test was used for statistical analysis of differences in miRNA expression between groups.

Example 2 miRnome Analysis of Breast Cancer Cell Lines with Different HER2/MSN Status

Materials and Methods

MiRNA expression levels in samples were quantified by quantitative RT-PCR (RT-qPCR) using the SYBR Green Master Mix kit on the ABI Prism 7900 Sequence Detection System as detailed in Example 1. Briefly, the Human miScript Primer Assays version 9.0 and 11.0 from Qiagen, designed to detect 804 human miRNA probes, were used according to the manufacturer's guidelines. The relative expression level of each miRNA, expressed as N-fold difference in target miRNA expression relative to RNU44. The relative expression of each miRNA was characterized by the median and the range, and a non-parametric Mann-Whitney test was used for statistical analysis of differences in miRNA expression between groups.

Figure 1:
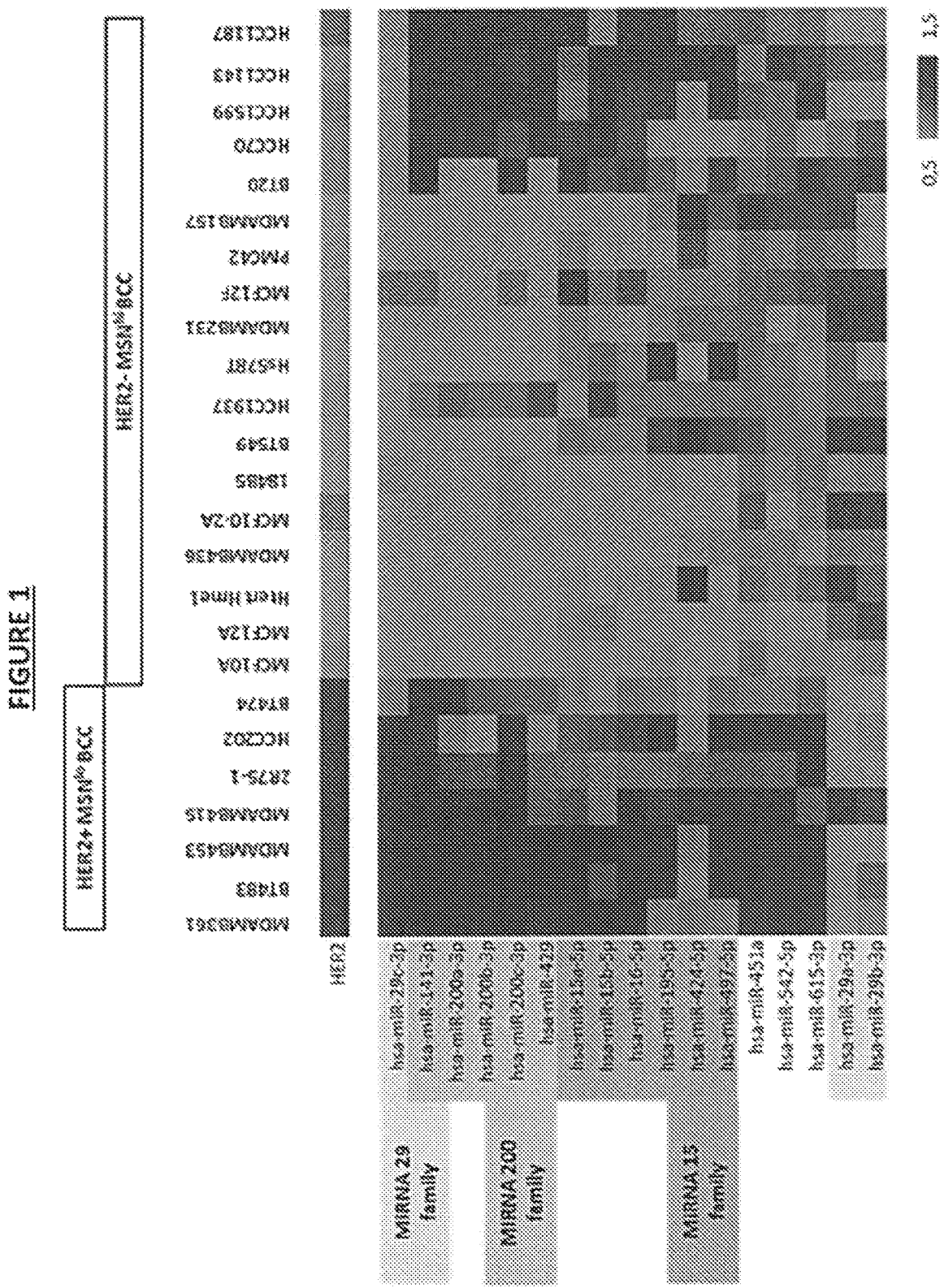

Results miRnome analysis of the 25 breast cancer cell lines identified several miRNAs that were differentially expressed in HER2+ breast cancer cell lines compared to HER2− breast cancer cell lines, among which the miRNA 29 family (miRNA 29a-3p, miRNA 29b-3p and miRNA 29c-3p), the 5 members of miR200 family (miRNA 200a-3p, miRNA 200b-3p, miRNA 200c-3p, miRNA 141-3p and miRNA 429-3p), the 6 members of miR15 family (miRNA 15a-5p, miRNA 15b-5p, miRNA 16-5p, miRNA 195-5p, miRNA 424-5p and miRNA 497-5p) as well as miRNA 451a-3p, miRNA 542-5p and miRNA 615-3p (FIG. 1). The results are detailed in Table 2 below.

| Family | miRNA | Fold increase | P value | |
|---|---|---|---|---|
| | hsa-miR-29c-3p | 7.2 | <0.0001 | *** |
| 29 | hsa-miR-29a-3p | 0.5 | 0.0124 | * |
| | hsa-miR-29b-3p | 0.7 | 0.1566 | ns |
| | hsa-miR-141-3p | 4.5 | <0.0001 | *** |
| | hsa-miR-200a-3p | 3.1 | 0.0082 | ** |
| 200 | hsa-miR-200b-3p | 2.8 | 0.0184 | * |
| | hsa-miR-200c-3p | 3.5 | 0.0002 | ** |
| | hsa-miR-429-3p | 2.3 | 0.0539 | ns |
| | hsa-miR-15a-5p | 2.3 | 0.037 | * |
| | hsa-miR-15b-5p | 1.3 | 0.3324 | ns |
| 15 | hsa-miR-16-5p | 2.3 | 0.0018 | ** |
| | hsa-miR-195-5p | 2.4 | 0.0231 | * |
| | hsa-miR-424-5p | 0.9 | 0.8105 | ns |
| | hsa-miR-497-5p | 2.6 | 0.0033 | ** |
| | hsa-miR-451a-3p | 1.5 | 0.0007 | ** |
| | hsa-miR-542-5p | 2.4 | <0.0001 | *** |
| | hsa-miR-615-3p | 1.8 | 0.001 | * |

Conclusion

The amount of key miRNAs (miRNA 29c-3p, miRNA 141-3p, miRNA 200a-3p, miRNA 200b-3p, miRNA 200c-3p, miRNA 429-3p, miRNA 15a-5p, miRNA 16-5p, miRNA 195-5p, miRNA 497, miRNA 615-3p, miRNA 451a-3p and miRNA 542-5p) was specifically increased in HER2+ breast cancer cell lines compared to HER2− breast cancer cell lines.

The amount of key miRNAs (miRNA 29a-3p, miRNA 29b-3p) was specifically decreased in HER2+ breast cancer cell lines compared to HER2− breast cancer cell lines These results confirmed that the above mentioned miRNA are relevant biomarkers in a method for diagnosing and/or prognosticating HER2-dependent cancer in a subject.

Example 3 miRNA 29 Family Correlated Survival

Materials and Methods

The effect of miRNA 29 family level of expression on the overall survival of breast cancer patients was measured using the online miRpower Kaplan-Meier plotter (http://kmplot.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ ER) or performed on HER2− (Triple negative breast cancers (TNBC) molecular subtype) breast cancer patients.

Results

Figure 2:
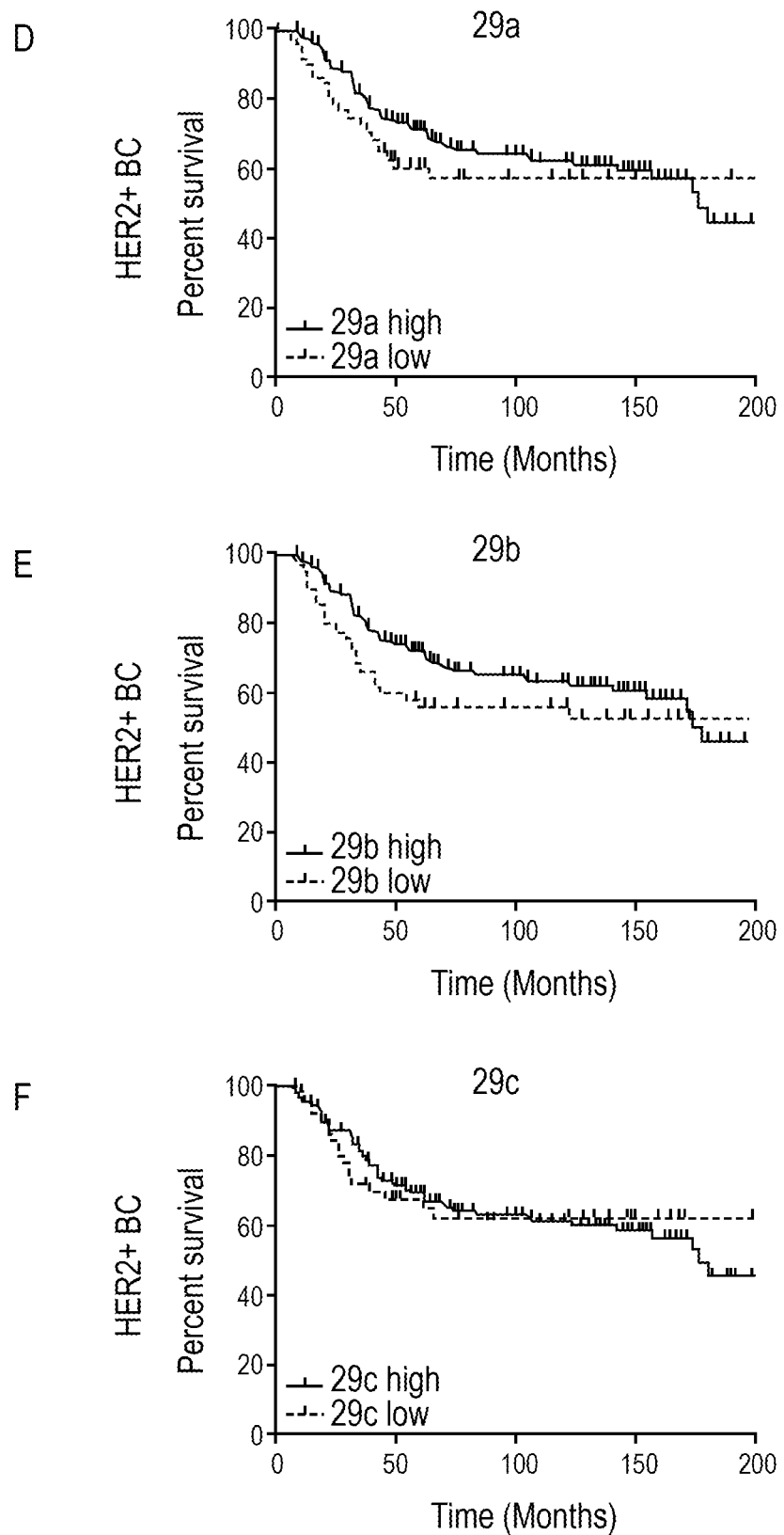
FIG. 2 represents the survival analyses of patients with HER2+ breast cancer (CDS HER2+) or HER2− breast cancer (CDS HER2−) depending on miRNA 29 family level of expression (miRNA 29a-3p, miRNA 29b-3p and miRNA 29c-3p). BC means Breast Cancer.

Low expression levels of miRNA 29a-3p and miRNA 29b-3p (downregulated in HER2+/MSN$^{lo}$ breast cancer cell lines, see Example 2) were associated with a trend towards shorter overall survival compared to patients having high expression levels of these miRNAs (FIG. 2A-B).

M/R29a-3p:
Median survival: 61 months with low expression level of miRNA 29a-3p vs. more than 200 months with high expression level of miRNA 29a-3p,
Overall survival: more than 70% death with low expression level of miRNA 29a-3p compared to less than 40% death with high expression level of miRNA 29a-3p (P=0.11).

MiR29b-3p:
Median survival: 73 months with low expression levels of miRNA 29b vs. more than 200 months with high expression level of miRNA 29b
Overall survival: more than 60% death with low expression level of miRNA 29b-3p compared to less than 40% death with high expression level of miRNA 29b-3p (P=0.59).

A similar trend was observed for HER2− breast cancer patients (P=0.38 and 0.17) (FIG. 2D-E).

On the contrary, high expression level of miRNA 29c-3p (upregulated in HER2+/MSN$^{lo}$ breast cancer cell lines, see Example 1) were associated with a trend towards shorter overall survival compared to patients having low expression level of this miRNA (FIG. 2C):

Median survival: 71 months with high expression level of miRNA 29c-3p vs. more than 200 months with low expression levels of miRNA 29c-3p
Overall survival: more than 55% death with high expression level of miRNA 29c-3p compared to less than 40% death with low expression level of miRNA 29c-3p (P=0.37)).

This trend was specific of HER2+ breast cancers, since level of expression of these miRNAs did not alter survival profiles of HER2− breast cancer patients (P=0.96) (FIG. 2F).

Conclusion

Survival analyses demonstrated that, the contrary to miRNA29a-3p and miRNA 29b-3p, higher amounts of miRNA29c-3p were associated with a shorter overall survival specifically among patients diagnosed with a HER2+ breast cancer.

These results confirmed that the above mentioned miRNA are relevant biomarkers for diagnosing and/or prognosticating HER2-dependent cancer in a subject.

Example 4 miRNA 200 Family Correlated Survival

Materials and Methods

The effect of miRNA 200 family level of expression on the overall survival of breast cancer patients was measured using the online miRpower Kaplan-Meier plotter (http://kmplot.com/analysis/index. php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ ER) or performed on HER2− (Triple negative breast cancers (TNBC) molecular subtype) breast cancer patients.

Results

Figure 3:
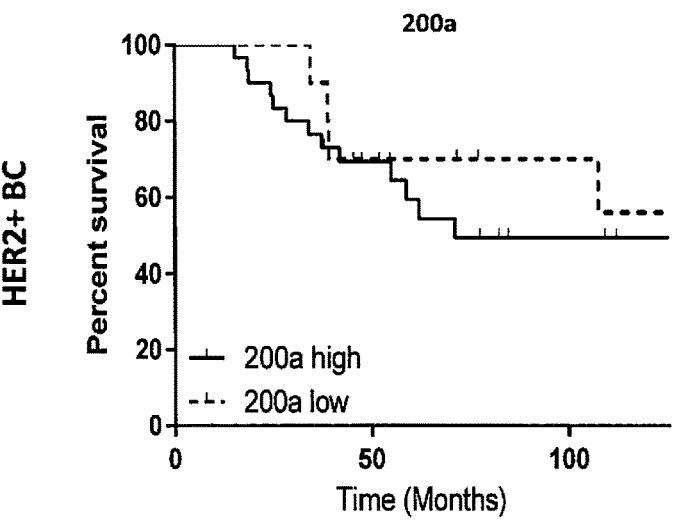
FIG. 3 represents the survival analyses of patients with HER2+ breast cancer (CDS HER2+) or HER2− breast cancer (CDS HER2−) depending on miRNA 200 family level of expression (miRNA 200a-3p, miRNA 200b-3p, miRNA 200c-3p, miRNA 141-3p and miRNA 429-3p). BC means Breast Cancer.
Figure 3:
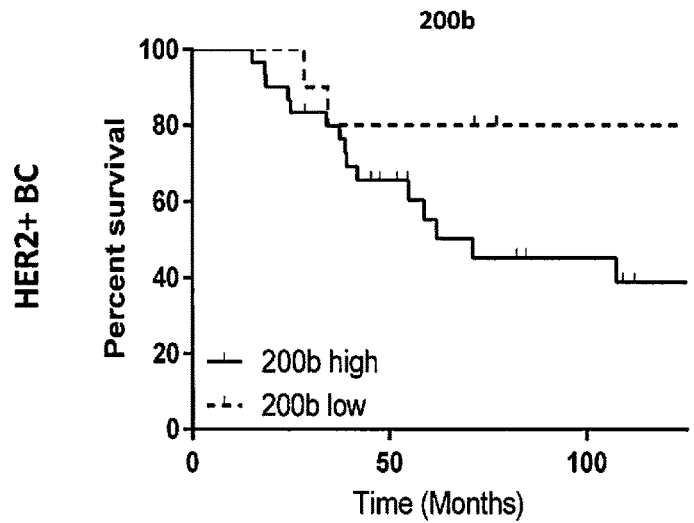
Figure 3:
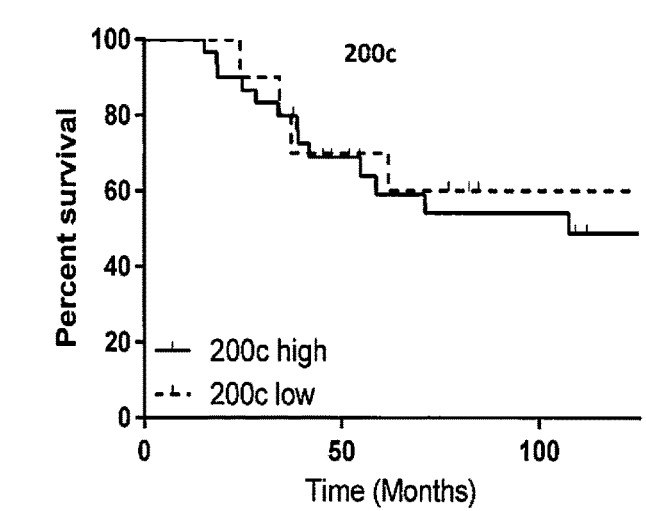
Figure 3:
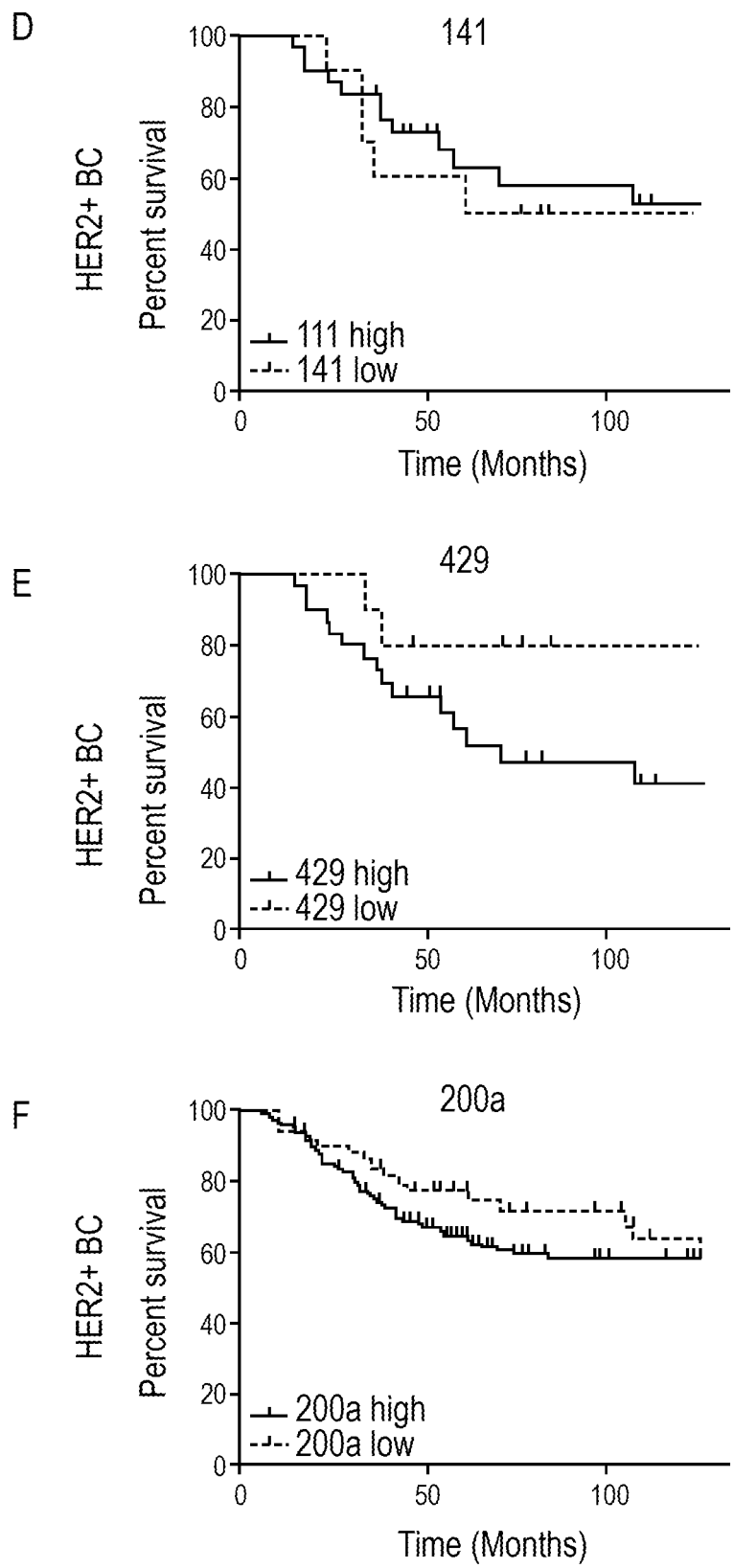
Figure 3:
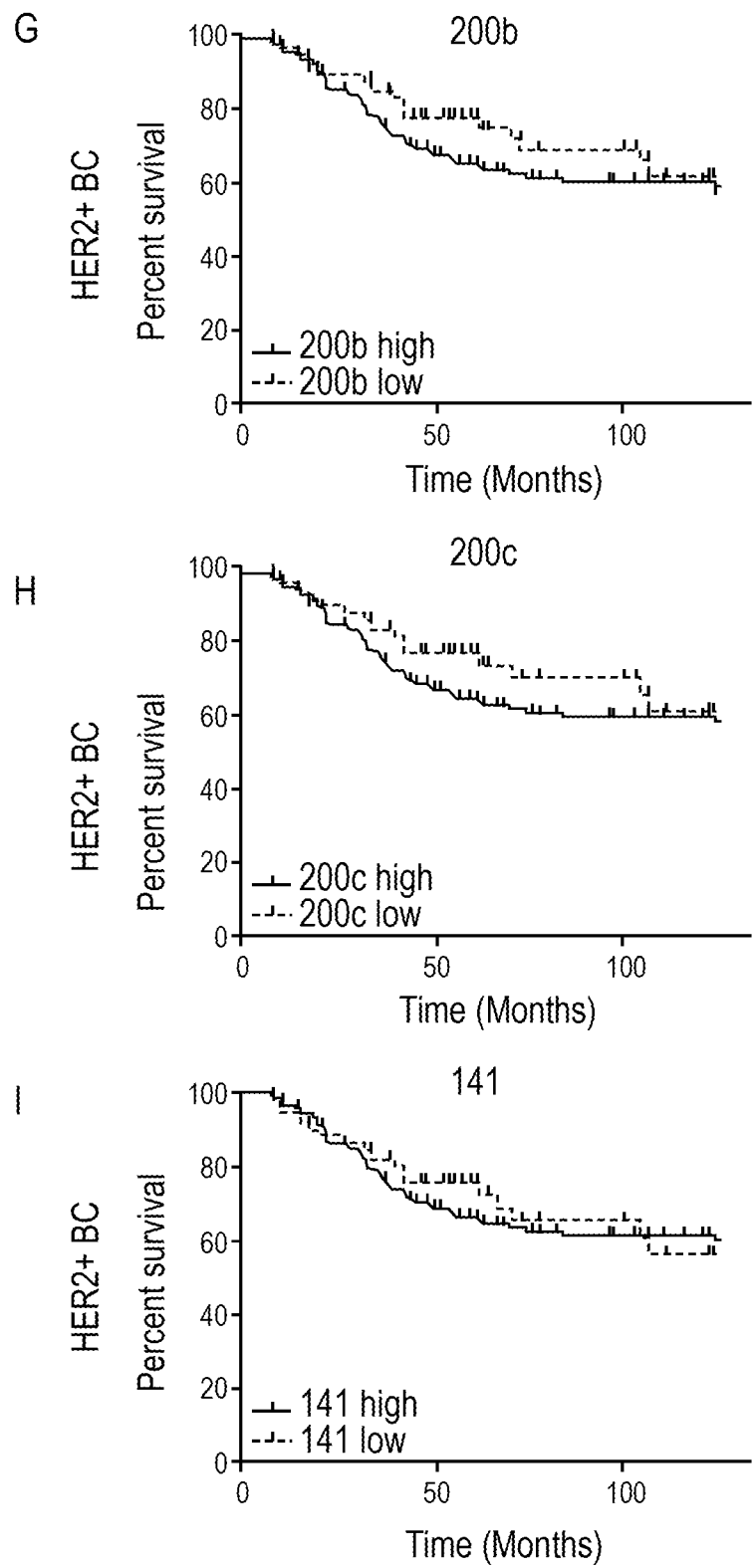
Figure 3:
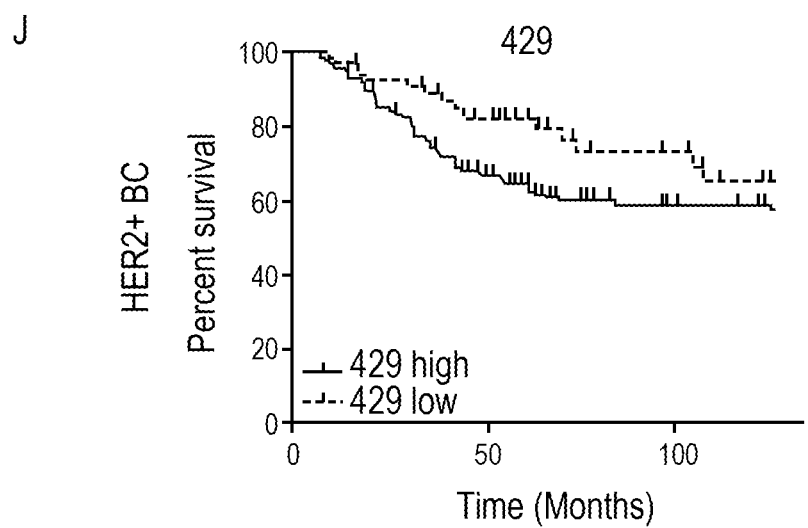

Among the 5 members of miR200 family, miR200a-3p (FIG. 3A, F), miRNA 200c-3p (FIG. 3C, H) and miRNA 141-3p (FIG. 3D, I) levels of expression did not significantly impacted patients' survival. On the contrary, high expression levels of miRNA 200b-3p and miRNA 429-3p were associated with a significantly shorter overall survival compared to patients having low expression level of these 2 miRNAs (FIG. 3B, E).

MIRNA 200b-3p:
Median survival: 62 months with high expression level of miRNA 200b-3p vs. more than 120 months with low expression level of miRNA 200b-3p,
Overall survival: 60% death with high expression level of miRNA 200b-3p compared to 20% with low expression level of miRNA 200b-3p (P=0.078).
MiRNA 429-3p:
Median survival: 62 months with high expression level of miRNA 429-3p vs. more than 120 with low expression level of miRNA 429-3p months,
Overall survival: 60% death with high expression level of miRNA 429-3p compared to 20% with low expression level of miRNA 200b-3p (P=0.09).

This trend was specific of HER2+ breast cancers since level of expression of these miRNAs did not significantly alter survival profiles of HER2− breast cancer patients (miRNA 200b-3p: P=0,38; miRNA 429-3p: P=0,13) (FIG. 3G, J).

Conclusion

Survival analyses demonstrated that higher amounts of miRNA 200b-3p and miRNA 429-3p were associated with a shorter overall survival specifically among patients diagnosed with a HER2+ breast cancer.

These results confirmed that the above mentioned miRNA are relevant biomarkers for diagnosing and/or prognosticating HER2-dependent cancer in a subject.

Example 5 miRNA 15 Family Correlated Survival

Materials and Methods

The effect of miRNA 15 family level of expression on the overall survival of breast cancer patients was measured using the online miRpower Kaplan-Meier plotter (http://kmplot.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ ER) or performed on HER2− (Triple negative breast cancers (TNBC) molecular subtype) breast cancer patients.

Results

Figure 4:
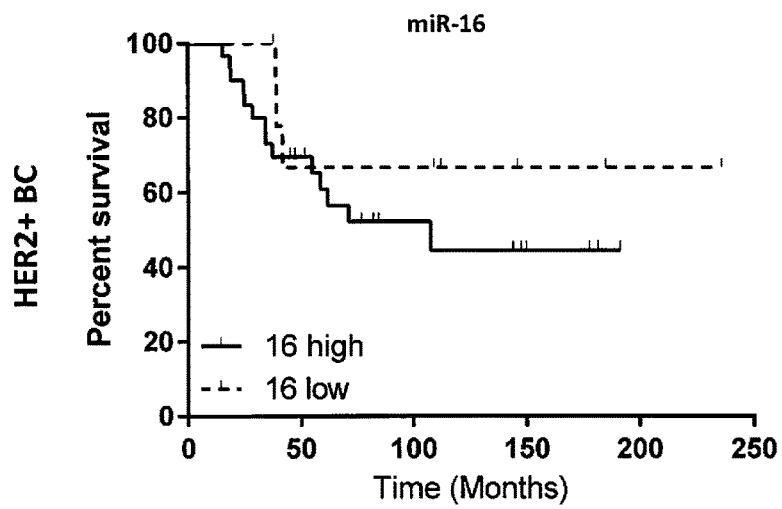
FIG. 4 represents the survival analyses of patients with HER2+ breast cancer (CDS HER2+) or HER2− breast cancer (CDS HER2−) depending on miRNA 15 family level of expression (miRNA 15a-5p, miRNA 15b-5p, miRNA 16-5p, miRNA 195-5p, miRNA 424-5p and miRNA 497-5p). BC means Breast Cancer.
Figure 4:
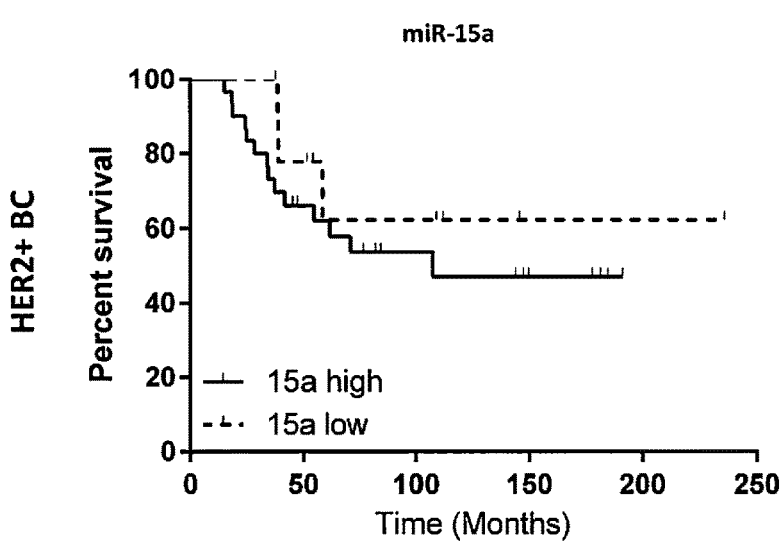
Figure 4:
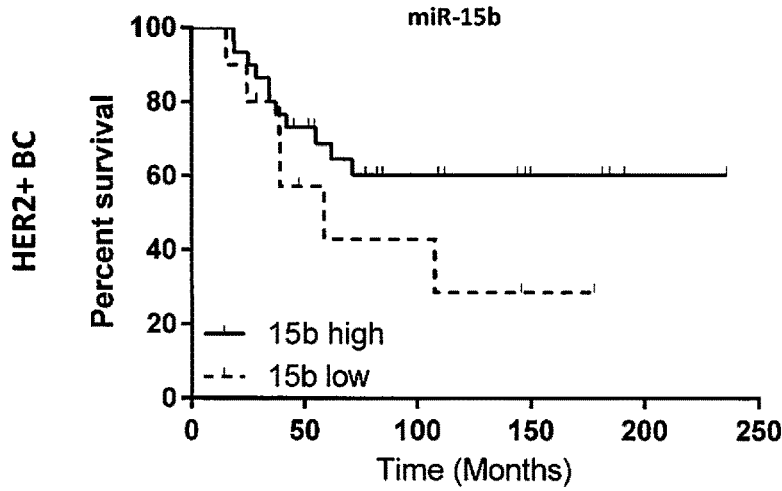
Figure 4:
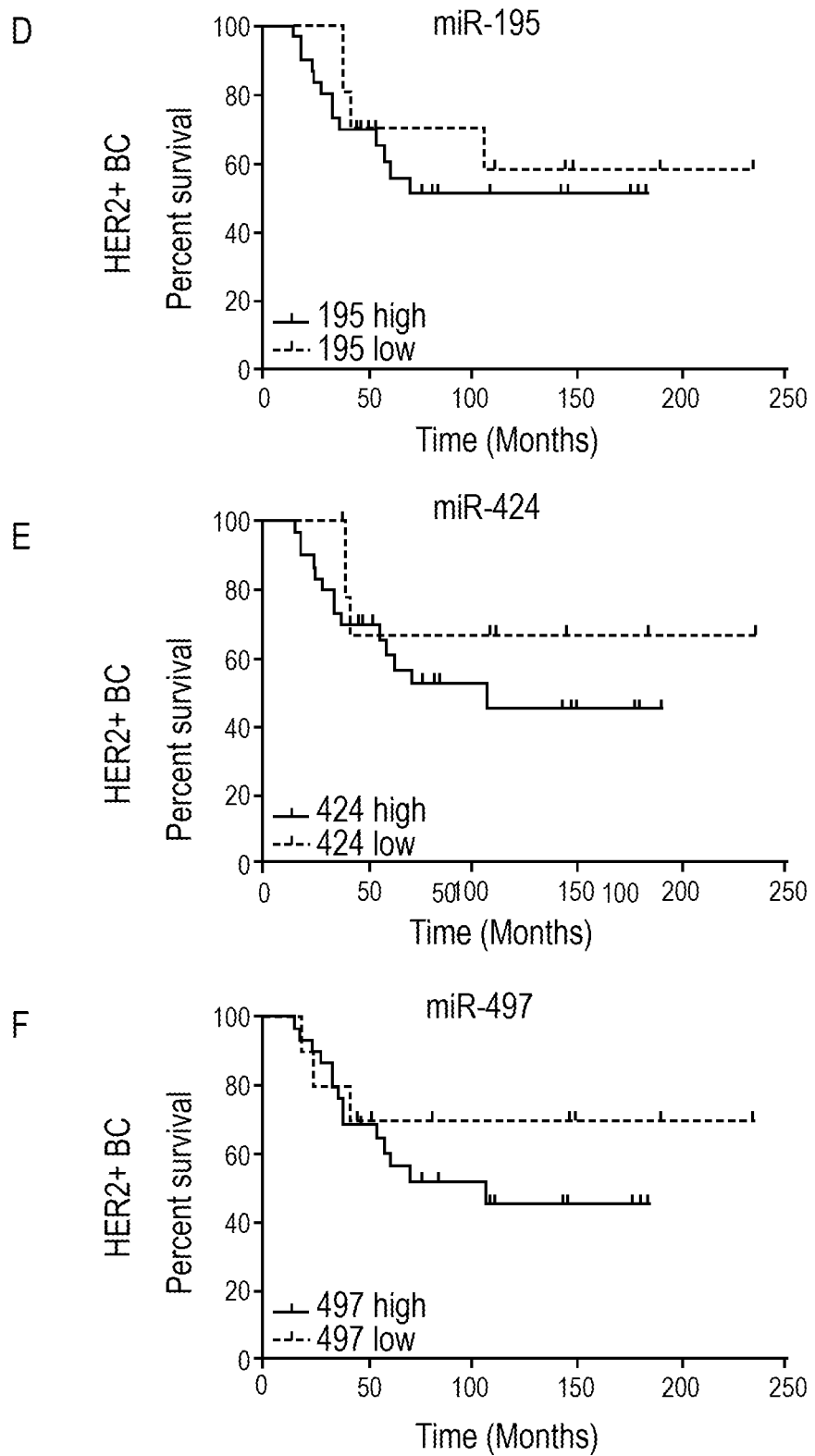
Figure 4:
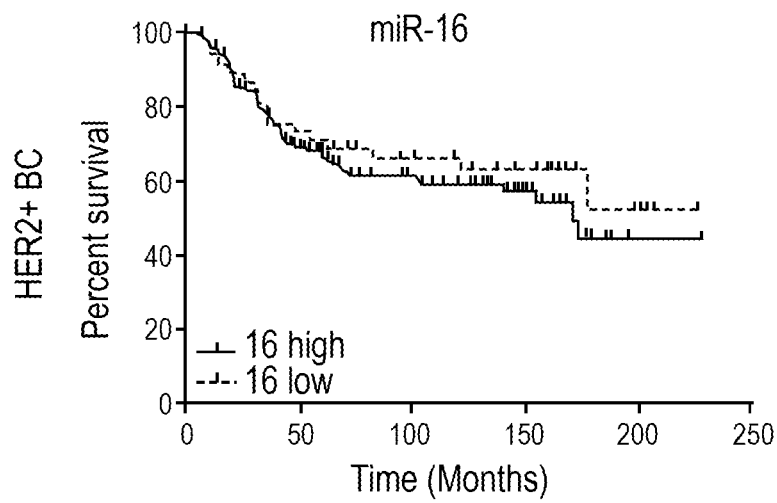
Figure 4:
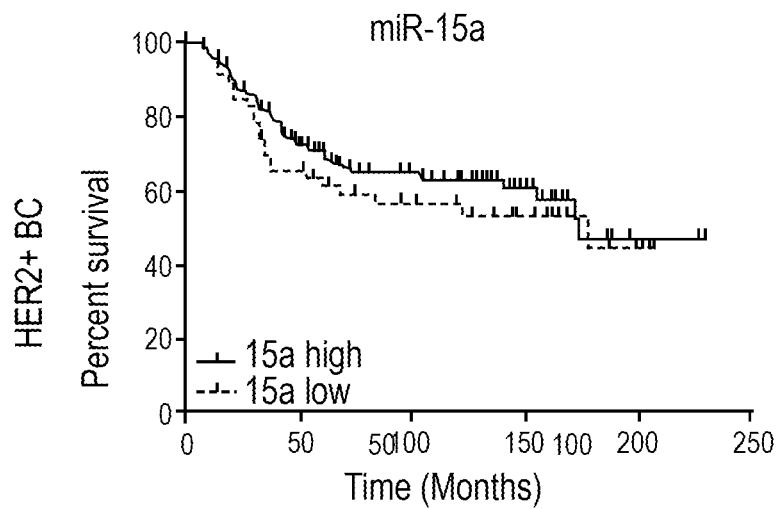
Figure 4:
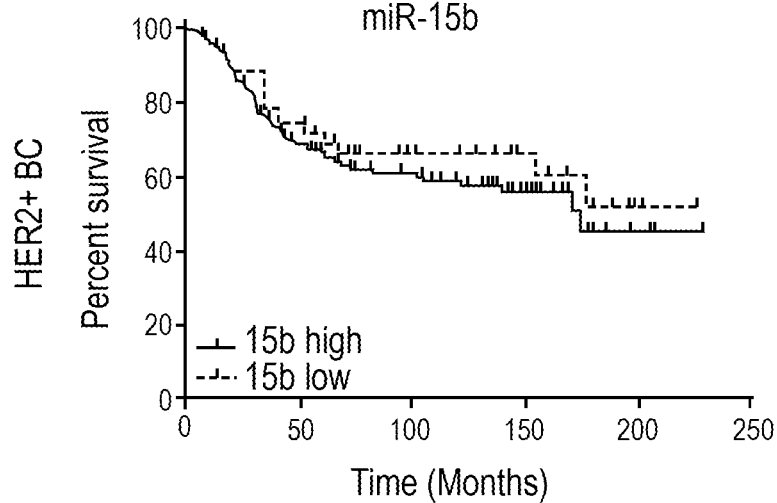
Figure 4:
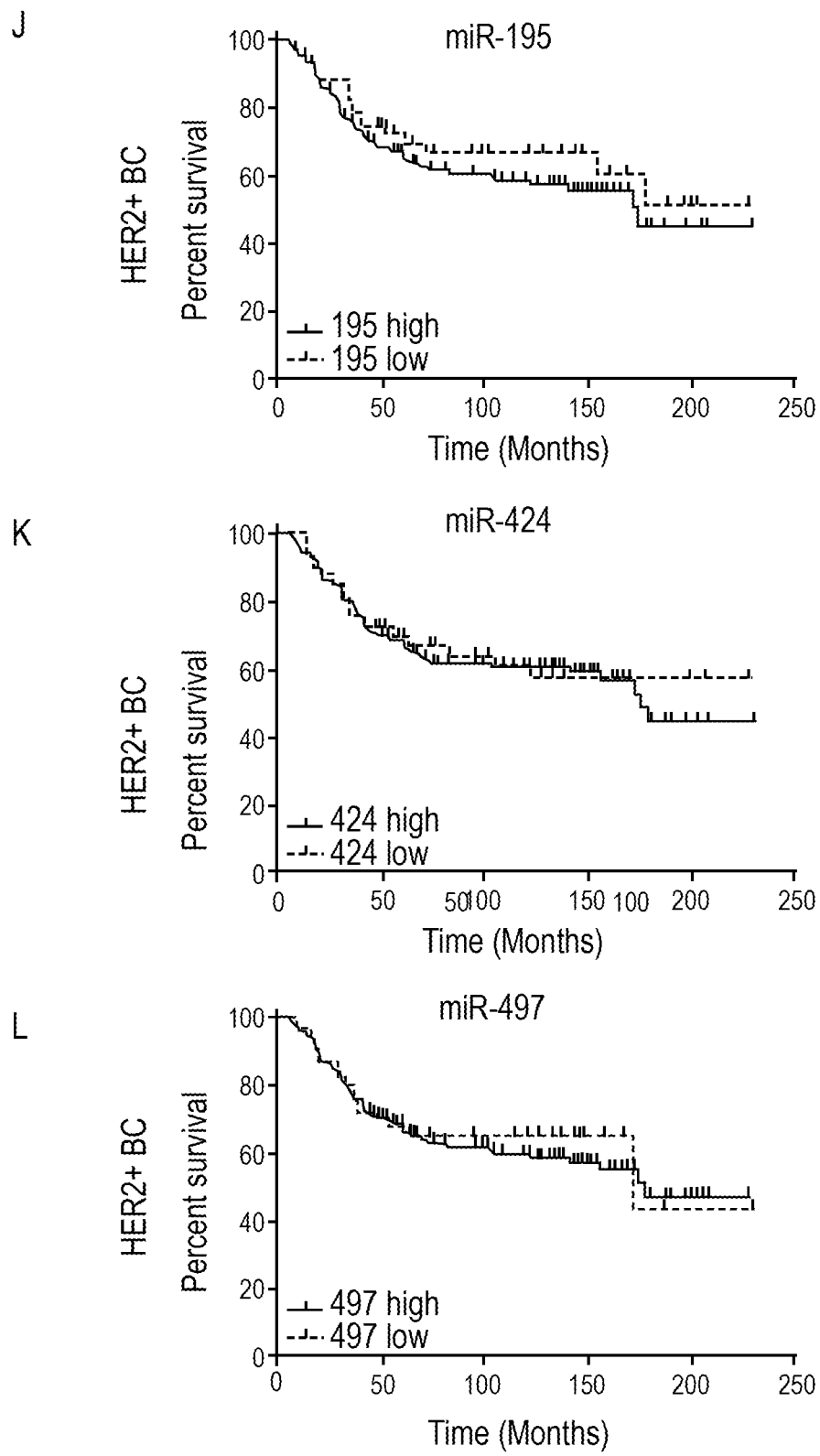

Among the 6 members of miRNA 15 family, high expression levels of miRNA 16-5p (FIG. 4A), miRNA 15a-5p (FIG. 4B), miRNA 424-5p (FIG. 4E) and miRNA 497-5p (FIG. 4F) were associated with a trend towards shorter overall survival compared to patients having low expression of these miRNAs.

MIRNA 16-5p:
Median survival: 107 months with high expression level of miRNA 16-5p vs. more than 200 months with low expression level of miRNA 16-5p,
Overall survival: more than 50% death months with high expression level of miRNA 16-5p compared to less than 40% death with low expression level of miRNA 16-5p (P=0.32).
MiRNA 15a-5p:
Median survival: 107 months with high expression level of miRNA 15a-5p vs. more than 200 months with low expression level of miRNA 15a-5p,
Overall survival: more than 50% death with high expression level of miRNA 15a-5p compared to less than 40% death with low expression level of miRNA 15a-5p (P=0.37).
MIRNA 424-5p:
Median survival: 108 months with high expression level of miRNA 424-5p vs. more than 200 months with low expression level of miRNA 424-5p,
Overall survival: more than 50% death with high expression level of miRNA 424-5p compared to less than 30% with low expression level of miRNA 424-5p (P=0.42).
MIRNA 497-5p:
Median survival: 108 months with high expression level of miRNA 497-5p vs. more than 200 months with low expression level of miRNA 497-5p,
Overall survival: more than 50% death with high expression level of miRNA 497-5p compared to less than 30% death with low expression level of miRNA 497-5p (P=0.42).

Moreover, miRNA 424-5p (FIG. 4K) and miRNA 497-5p (FIG. 4L) did not alter survival profiles of HER2− breast cancer patients (P=0.79 and 0.91). In HER2− breast cancer patients, high expression level of miRNA 15a-5p (FIG. 4H) was associated with a trend towards longer overall survival compared to patients having low expression level of this miRNA (P=0,38).

MiRNA 195-5p (FIG. 4D) expression level did not alter survival profiles of HER2+ breast cancer patients and low expression level of miRNA 15b-5p (FIG. 4C) that was not seen upregulated in the miRnome analysis of FIG. 1 were associated with a trend towards shorter overall survival compared to patients having high expression level of this miRNA (P=0.17).

Conclusion

Survival analyses demonstrated that higher amount of miRNA 16-5p, miRNA 15a, miRNA 424-5p and miRNA 497-5p were associated with a shorter overall survival specifically among patients diagnosed with a HER2+ breast cancer.

These results confirmed that the above mentioned miRNA are relevant biomarkers for diagnosing and/or prognosticating HER2-dependent cancer in a subject.

Example 6 miRNA 615-3p. miRNA 451a-3p and miRNA 542-5p Correlated Survival

Materials and Methods

The effect of miRNA 615-3p, miRNA 451a-3p and miRNA 542-5p on the overall survival of breast cancer patients was measured using the online miRpower Kaplan-Meier plotter (http://kmplot.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ ER) or performed on HER2− (Triple negative breast cancers (TNBC) molecular subtype) breast cancer patients.

Results

High levels of miRNA 451a-3p (FIG. 5B), mi-RNA 542-5p (FIG. 5C) and miRNA 615-3p (FIG. 5A) were associated with a significantly shorter overall survival compared to patients having low expression of these 3 miRNAs.

MIRNA 615-3p:

Median survival: 108 months with high expression level of miRNA 615-3p vs. more than 200 months with low expression level of miRNA 615-3p, Overall survival: more than 50% with high expression level of miRNA-615-3p death compared to less than 30% death with low expression level of miRNA 615-3p (P=0.54).

MIRNA 451a-3p:

Median survival: 108 months with high expression level of miRNA 451a-3p vs. more than 200 months with low expression level of miRNA 451a-3p, Overall survival: more than 50% death with high expression level of miRNA 451a-3p compared to less than 40% with low expression level of miRNA 451a-3p (P=0.26).

MIRNA 542-5p:

Median survival: 108 months with high expression level of miRNA 542-5p vs. more than 200 months with low expression level of miRNA 542-5p, Overall survival: more than 50% death with high expression level of miRNA 542-5p compared to less than 30% death with low expression level of miRNA 542-5p (P=0.31).

Figure 5:
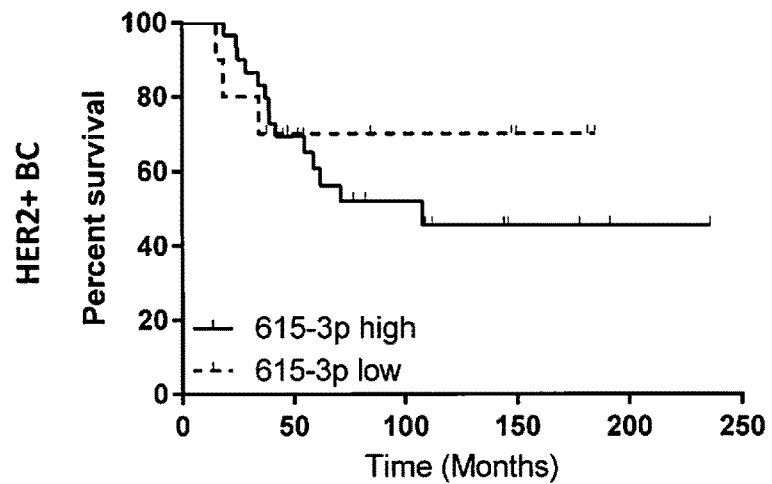
FIG. 5 represents the survival analyses of patients with HER2+ breast cancer (CDS HER2+) or HER2− breast cancer (CDS HER2−) depending on miRNA 615-3p, miRNA 451a-3p and miRNA 542-5p level of expression. BC means Breast Cancer.
Figure 5:
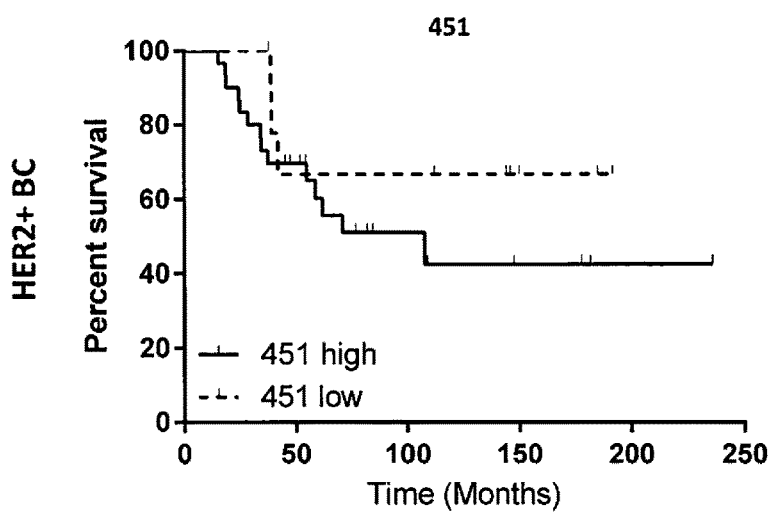
Figure 5:
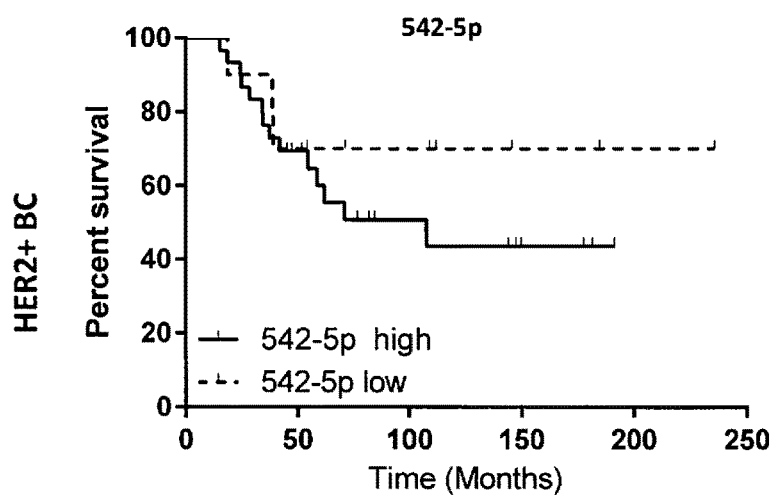
Figure 5:
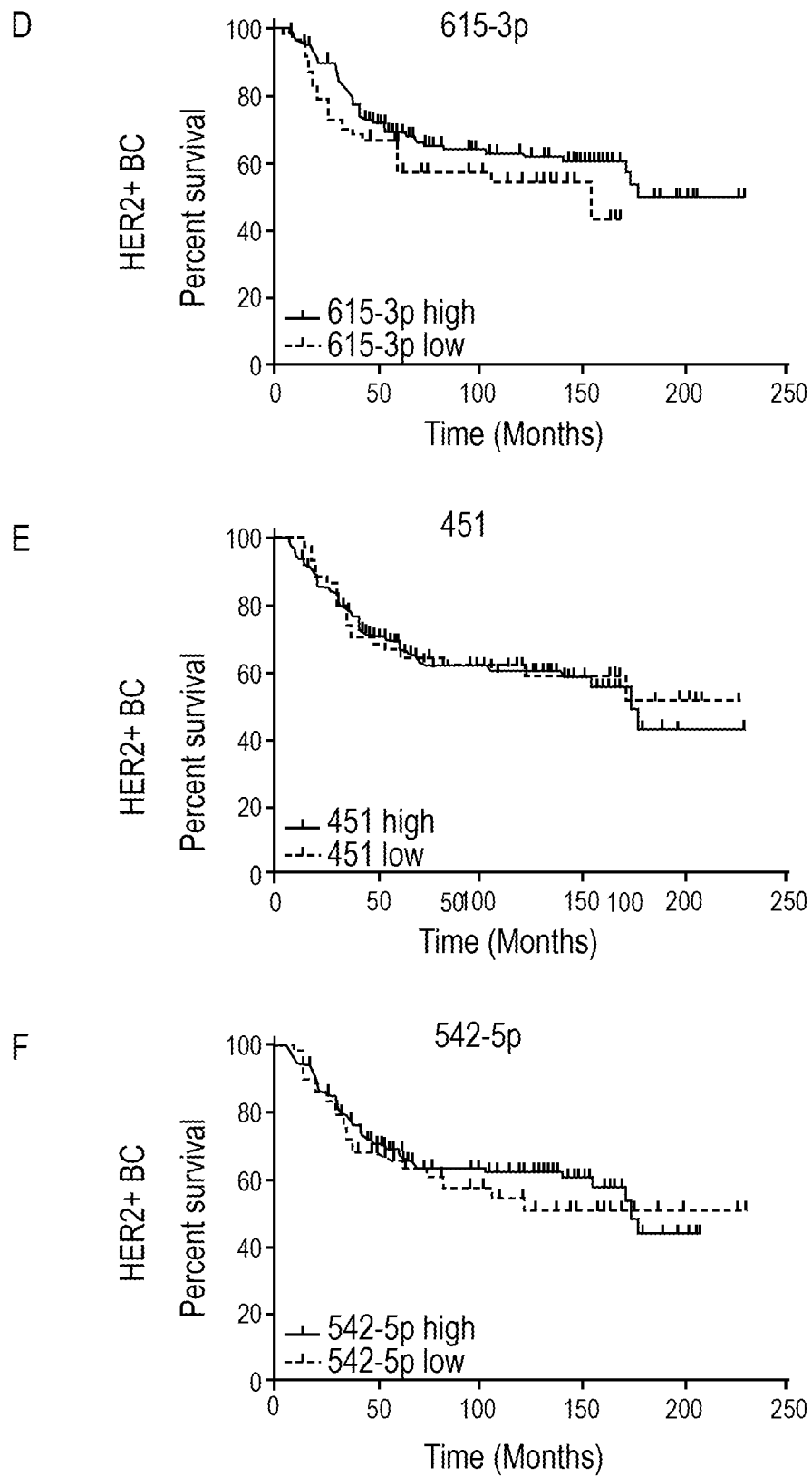

Their trends were specific of HER2+ breast cancers since levels of expression of these miRNAs did not necessarily alter survival profiles of HER2− breast cancer patients (FIG. 5D-F).

Conclusion

Survival analyses demonstrated that higher amount of miRNA 615-3p, miRNA 451a-3p and miRNA 542-5p were associated with a shorter overall survival specifically among patients diagnosed with a HER2+ breast cancer.

These results confirmed that the above mentioned miRNA are relevant biomarkers for diagnosing and/or prognosticating HER2-dependent cancer in a subject.

Example 7

Circulating miR-141-3p, miR-200a-3p, miR-200b-3p and miR-200c-3p Analysis of Breast Cancer Patients with Different HER2 Status and Healthy Volunteers Materials and Methods MiRNA expression levels in pre-operative serum samples quantified by qRT-PCR derived from healthy individuals (n=22), HER2+ breast cancer patients (n=14) or HER2− breast cancer patients (n=18) obtained from the study GSE42128 (Gene Expression Omnibus accession number) on array express database (http://www.ebi.ac.uk/arrayexpress/) were analyzed. The combined profile of their expression is the mean of their individual expression. Statistical analysis is a Kruskal-Wallis one-way anova test (P=0.0174; Dunn's multiple comparisons test: Healthy vs. HER2+ adjusted P=0,0255 *; Healthy vs. HER2− adjusted P>0,9999 ns; HER2+ vs. HER2− adjusted P=0,0463°) performed using GraphPad Prism software.

Results

Individual level of expression of miR-141-3p, miR-200a-3p, miR-200b-3p and miR-200c-3p in pre-operative serum samples of $HER2_+$ breast cancer patients (n=14) were found higher compared to HER2− breast cancer patients (n=18) or healthy controls (n=22). The combined expression level of miR-141-3p, miR-200a-3p, miR-200b-3p and miR-200c-3p is significantly higher in serum samples from HER2+ breast cancer patients than HER2− breast cancer patients (P=0255) or healthy controls (P=0,0463) (FIG. 6).

Conclusion

The combined amount of key miRNAs (miRNA 141-3p, miRNA 200a-3p and miRNA 200b-3p and miRNA 200c-3p) was significantly increased in the serum of HER2+ breast cancer patients compared to HER2− breast cancer patients and healthy individuals. Therefore, they represent very interesting biomarkers for non-invasive diagnosis of breast cancer.

These results confirmed that the above-mentioned miRNA are relevant biomarkers in a method for diagnosing and/or prognosticating HER2-dependent cancer in a subject.

The invention claimed is:

1. A method for prognosticating HER2-dependent cancer, comprising:
   a) measuring an amount of one or more miRNA selected from the group consisting of miRNA 429-3p, miRNA 29c-3p, miRNA 200b-3p, miRNA 15a-5p, miRNA 16-5p, miRNA 424-5p, miRNA 49'7-5p, miRNA 615-3p, miRNA 451a-3p and miRNA 542-5p in a sample from a subject diagnosed with HER2-dependent cancer;
   b) comparing the amount of one or more miRNA measured in step a) to a reference value;
   c) finding a deviation or no deviation of the amount of one or more miRNA measured in step a) from the reference value;
   d) attributing said finding of deviation or no deviation to a particular prognosis of HER2-dependent cancer in the subject; and
   e) administering to the subject an antitumoral treatment targeting the extracellular domain of HER2 or targeting a kinase activity of HER2 upon an indication that the subject has a poor prognosis.

2. The method according to claim 1, wherein a higher amount of one or more miRNA selected from the group consisting of miRNA 429-3p, miRNA 29c-3p, miRNA 200b-3p, miRNA 49'7-5p, miRNA 615-3p, miRNA 451a-3p, miRNA 542-5p, miRNA 15a-5p, miRNA 16-5p and miRNA 424-5p in the sample from the subject compared to the reference value indicates a short-term survival of said subject.

3. The method according to claim 1, wherein the sample is a tumor sample or a body fluid sample.

4. The method according to claim 3, wherein the body fluid sample is selected from the group consisting of blood, serum plasma, saliva and urine, amniotic fluid, breast milk, bronchial lavage, cerebrospinal fluid, peritoneal fluid, seminal fluid, tears and pleural fluid.

5. The method according to claim 2, wherein the amount of the one or more miRNA in the sample from the subject is at least 1.5 fold increased compared to the reference value, more preferably at least 2 fold increased.

6. The method according to claim 1, wherein the reference value represents a good prognosis or a bad prognosis of HER2-dependent cancer.

7. The method according to claim 1, wherein step a) comprises measuring the amount of the one or more miRNA by employing a PCR-based detection method.

8. The method according to claim 1, wherein the HER2-dependent cancer is selected from the group consisting of breast cancer, female genital tract cancer, such as endometrial cancer, uterine cancer or ovarian cancer, bladder cancer, anal cancer, colorectal cancer, in particular uterine serous cancer, such as uterine papillary serous carcinoma, lung cancer, in particular non-small-cell lung cancer, liver cancer, kidney cancer, gastroesophageal cancer, stomach cancer, pancreas cancer and gastric cancer.

9. The method according to claim 1, wherein said HER2-dependent cancer is HER2+ breast cancer.

10. A method for monitoring a change in prognosis of HER2-dependent cancer in a subject, comprising:
   a) applying the method of claim 1 to the subject at one or more successive time points, whereby the prognosis of HER2-dependent cancer in the subject is determined at said successive time points;
   b) comparing the prognosis of HER2-dependent cancer in the subject at said successive time points as determined in step a);
   c) finding the presence or absence of a change between the diagnosis of HER2-dependent cancer in the subject at said successive time points as determined in step a); and
   d) administering to the subject an antitumoral treatment targeting the extracellular domain of HER2 or targeting a kinase activity of HER2 upon an indication that the subject has a poor prognosis at the one or more successive time points.

11. The method according to claim 10, wherein said change in the prognosis of HER2-dependent cancer in the subject is monitored in the course of a medical treatment of said subject.

12. The method according to claim 11, wherein the medical treatment is a prophylactic treatment or a therapeutic treatment.

13. The method of claim 1, wherein targeting the extracellular domain of HER2 comprises the administration of Herceptin/Trastuzumab, Pertuzumab and/or Trastuzumab emtansine to the subject.

14. The method of claim 1, wherein targeting the kinase activity of HER2 comprises the administration of a small molecule tyrosine kinase inhibitor to the subject.

15. The method of claim 14, wherein the small molecule tyrosine kinase inhibitor is Neratinib, Tucatinib and/or Lapatinib/Tykerb.

* * * * *

SEQUENCE LISTING

```
<160> NUMBER OF SEQ ID NOS: 16

<210> SEQ ID NO 1
<211> LENGTH: 22
<212> TYPE: RNA
<213> ORGANISM: Homo sapiens

<400> SEQUENCE: 1
uagcaccauc ugaaaucggu ua                                        22

<210> SEQ ID NO 2
<211> LENGTH: 22
<212> TYPE: RNA
<213> ORGANISM: Homo sapiens

<400> SEQUENCE: 2
uagcaccauu ugaaaucggu ua                                        22

<210> SEQ ID NO 3
<211> LENGTH: 22
<212> TYPE: RNA
<213> ORGANISM: Homo sapiens
```

-continued

```
<400> SEQUENCE: 3
uagcaccauc ugaaaucggu ua                                          22

<210> SEQ ID NO 4
<211> LENGTH: 23
<212> TYPE: RNA
<213> ORGANISM: Homo sapiens

<400> SEQUENCE: 4
uagcaccauu ugaaaucagu guu                                         23

<210> SEQ ID NO 5
<211> LENGTH: 22
<212> TYPE: RNA
<213> ORGANISM: Homo sapiens

<400> SEQUENCE: 5
uaacacuguc ugguaacgau gu                                          22

<210> SEQ ID NO 6
<211> LENGTH: 22
<212> TYPE: RNA
<213> ORGANISM: Homo sapiens

<400> SEQUENCE: 6
uaauacugcc ugguaaugau ga                                          22

<210> SEQ ID NO 7
<211> LENGTH: 23
<212> TYPE: RNA
<213> ORGANISM: Homo sapiens

<400> SEQUENCE: 7
uaauacugcc ggguaaugau gga                                         23

<210> SEQ ID NO 8
<211> LENGTH: 22
<212> TYPE: RNA
<213> ORGANISM: Homo sapiens

<400> SEQUENCE: 8
uaacacuguc ugguaaagau gg                                          22

<210> SEQ ID NO 9
<211> LENGTH: 22
<212> TYPE: RNA
<213> ORGANISM: Homo sapiens

<400> SEQUENCE: 9
uagcagcaca uaaugguuug ug                                          22

<210> SEQ ID NO 10
<211> LENGTH: 22
<212> TYPE: RNA
<213> ORGANISM: Homo sapiens

<400> SEQUENCE: 10
uagcagcaca ucaugguuua ca                                          22

<210> SEQ ID NO 11
<211> LENGTH: 22
<212> TYPE: RNA
<213> ORGANISM: Homo sapiens
```

```
<400> SEQUENCE: 11
uagcagcacg uaaauauugg cg                                          22

<210> SEQ ID NO 12
<211> LENGTH: 22
<212> TYPE: RNA
<213> ORGANISM: Homo sapiens

<400> SEQUENCE: 12
cagcagcaau ucauguuuug aa                                          22

<210> SEQ ID NO 13
<211> LENGTH: 21
<212> TYPE: RNA
<213> ORGANISM: Homo sapiens

<400> SEQUENCE: 13
cagcagcaca cugugguuug u                                           21

<210> SEQ ID NO 14
<211> LENGTH: 22
<212> TYPE: RNA
<213> ORGANISM: Homo sapiens

<400> SEQUENCE: 14
uccgagccug ggucucccuc uu                                          22

<210> SEQ ID NO 15
<211> LENGTH: 22
<212> TYPE: RNA
<213> ORGANISM: Homo sapiens

<400> SEQUENCE: 15
aaaccguuac cauuacugag uu                                          22

<210> SEQ ID NO 16
<211> LENGTH: 23
<212> TYPE: RNA
<213> ORGANISM: Homo sapiens

<400> SEQUENCE: 16
ucggggauca ucaugucacg aga                                         23
```